United States Patent
Takemura et al.

(10) Patent No.: US 6,656,952 B2
(45) Date of Patent: *Dec. 2, 2003

(54) CIS-SUBSTITUTED FLUOROMETHYLPYRROLIDINE DERIVATIVE

(75) Inventors: Makoto Takemura, Tokyo (JP); Hisashi Takahashi, Tokyo (JP); Hitoshi Ohki, Tokyo (JP); Kenichi Kimura, Tokyo (JP); Rie Miyauchi, Tokyo (JP); Toshiyuki Takeda, Tokyo (JP)

(73) Assignee: Daiichi Pharmaceutical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 122 days.

(21) Appl. No.: 09/446,696

(22) PCT Filed: Jun. 23, 1998

(86) PCT No.: PCT/JP98/02787

§ 371 (c)(1),
(2), (4) Date: Dec. 23, 1999

(65) Prior Publication Data

US 2002/0072608 A1 Jun. 13, 2002

(30) Foreign Application Priority Data

Jun. 24, 1997 (JP) ............................ P.9-166438
Mar. 6, 1998 (JP) ........................ P.10-054700

(51) Int. Cl.$^7$ ..................... A61K 31/47; C07D 215/16; C07D 207/10
(52) U.S. Cl. ................. 514/312; 546/156; 548/557
(58) Field of Search ................ 514/312; 546/156; 548/557

(56) References Cited

FOREIGN PATENT DOCUMENTS

| JP | 62-19583 | 1/1987 | ......... C07D/401/04 |
|----|----------|--------|-----------------------|
| JP | 63-45261 | 2/1988 | ......... C07D/215/56 |
| JP | 63-51370 | 3/1988 | ......... C07D/207/14 |
| JP | 63-152318 | 6/1988 | ......... A61K/31/47 |
| JP | 3-188074 | 8/1991 | ......... C07D/401/04 |
| JP | 8-277284 | 10/1996 | ......... C07D/401/04 |
| JP | 9-67368 | 3/1997 | ......... C07D/401/04 |
| JP | 9-136886 | 5/1997 | ......... C07D/401/04 |

OTHER PUBLICATIONS

Suto M J et al: "Fluoroquinolones: Relationships Between Structural Variations, Mammalian Cell Cytotoxicity, and Antimicrobial Activity" Journal of Medicinal Chemistry, U.S. American Chemical Society, Washington, vol. 35, No. 25, 1992, pp. 4745–4750.

John M. Domagala: "Structure–activity and structure–side–effect relationship for the quinolone antibacterials" Journal of Antimocrobial Chemotherapy, vol. 33, 1994, pp. 685–706.

Chemical Abstracts 109:92775, abstracts of JP 63051370, Hirose, 1988.*

* cited by examiner

Primary Examiner—D. Margaret Seaman
(74) Attorney, Agent, or Firm—Sughrue Mion, PLLC

(57) ABSTRACT

An antibacterial drug having potent antibacterial activities upon various bacteria including resistant strains and high safety is disclosed, which comprises as an active ingredient, quinolone derivatives represented by the following formula (I), its salts or hydrates thereof:

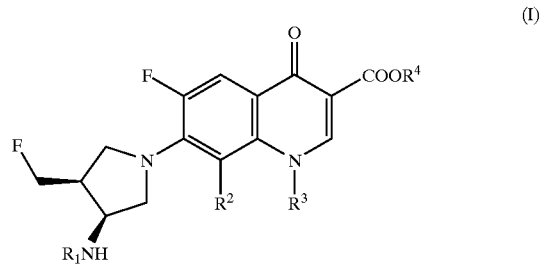

(I)

wherein $R^1$ represents a hydrogen atom or an alkyl group having 1 to 6 carbon atoms, $R^2$ represents a halogenomethoxyl group or an alkoxyl group, $R^3$ represents an alkyl group, an alkenyl group, a halogenoalkyl group, a cyclic alkyl group, a heteroaryl group, an alkoxyl group or an alkylamino group, and $R^4$ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, 3-acetoxy-2-oxobutyl group, an alkyl group, an alkoxylmethyl group or a phenylalkyl group. These substituents may further have additional substituents.

13 Claims, No Drawings

CIS-SUBSTITUTED FLUOROMETHYLPYRROLIDINE DERIVATIVE

TECHNICAL FIELD

This invention relates to an 8-(substituted)alkoxy-4-oxoquinoline-3-carboxylic acid derivative having 3-(S)-amino-4-(S)-fluoromethylpyrrolidin-1-yl group at the 7-position of the quinoline nucleus as a substituent, which has excellent antibacterial activity, good pharmacokinetics and high safety, and to an antibacterial agent and an antibacterial preparation, which contain the compound.

This invention also relates to a compound which is useful for introducing a substituent at the 7-position that has such a structure that excellent antibacterial activity, pharmacokinetics and safety can be added to synthetic quinolone antibacterial agents in which the structure of the substituent at the 7-position exerts important influences upon the antibacterial activity, pharmacokinetics and safety.

BACKGROUND ART

Since the discovery of norfloxacin, antibacterial activity and pharmacokinetics of quinolone synthetic antibacterial agents have been improved, and many compounds are now used in the clinical field as chemotherapeutic agents which are effective in almost systemic infectious diseases.

In recent years, generation of bacteria having low sensitivity to quinolone synthetic antibacterial agents has been increasing in the field of clinics. For example, like the case of *Staphylococcus aureus* (MRSA) which is non-sensitive to β-lactam antibiotics, a case has been increasing in which a bacterium originally resistant to drugs other than quinolone synthetic antibacterial agents becomes low-sensitive to quinolone synthetic antibacterial agents too. In consequence, development of a drug having further high efficacy has been called for in the field of clinics. On the other hand, it has been revealed that quinolone synthetic antibacterial agents cause a side effect in which severe convulsion is induced when a non-steroidal anti-inflammatory drug is simultaneously used, as well as other side effects such as phototoxicity and the like, so that development of a quinolone synthetic antibacterial agent having higher safety has also been called for in the field.

Quinolone-carboxylic acid derivatives which has the cis-3-amino-4-fluoromethylpyrrolidin-1-yl group related to the present invention as a substituent are disclosed for example in JP-A-62-19583, JP-A-63-45261 and JP-A-63-152318 (the term "JP-A" as used herein means an "unexamined published Japanese patent application"), and these patents describe compounds represented by the following formula. However, though the substituent at the 7-position of these disclosed quinolones is a cis-3-amino-4-fluoromethylpyrrolidin-1-yl group, they are compounds which have the 8-fluoroquinoline nucleus in which the 8-position substituent is a halogen atom, and nothing is described about a compound which has the 8-methoxyquinoline nucleus related to the present invention. In addition, there is no illustrative disclosure in these specifications concerning an optically active compound 3-(S)-amino-4-(S)-fluoromethylpyrrolidine or 3-(S)-amino-4-(S)-fluoromethylpyrrolidinyl group.

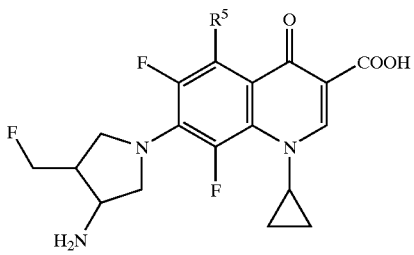

(In the above formula, $R^5$ is a hydrogen atom or a fluorine atom. Definition of the substituent of the compound represented by the formula (III) is unrelated to the compound of the present invention.)

In addition, JP-A-3-188074 discloses a compound represented by the following formula (IV), but it does not disclose a compound which has the 1-cyclopropyl-8-methoxyquinoline nucleus related to the present invention. Also, there is no illustrative disclosure in the specification concerning an optically active compound 3-(S)-amino-4-(S)-fluoromethylpyrrolidine or 3-(S)-amino-4-(S)-fluoromethylpyrrolidinyl group.

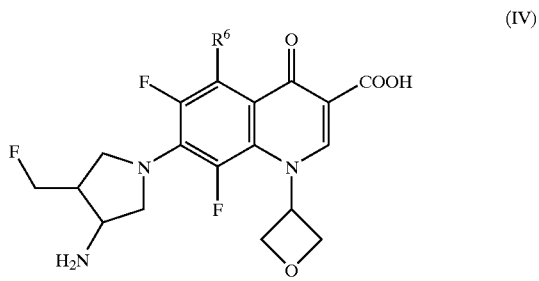

(In the above formula, $R^6$ is a hydrogen atom or an amino group. Definition of the substituent of the compound represented by the formula (IV) is unrelated to the compound of the present invention.)

Also, JP-A-4-211077 discloses a compound which has the 1-cyclopropyl-8-methoxyquinoline nucleus, represented by the following formula (V). However, there is no illustration in the specification concerning a compound substituted with 3-(S)-amino-4-(S)-fluoromethylpyrrolidinyl group.

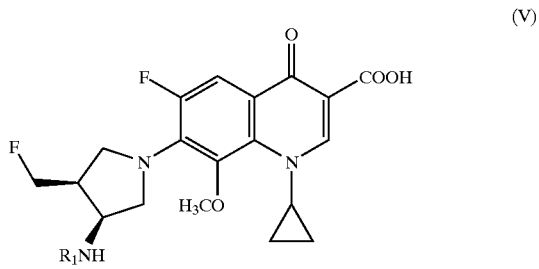

(In the above formula, $R^7$ is methyl, ethyl or the like lower alkyl group. Definition of the substituent of the compound represented by the formula (V) is unrelated to the compound of the present invention.)

In addition, there is no description in the just described specification about safety of a compound represented by the following formula (VI) in which $R^7$ is a methyl group.

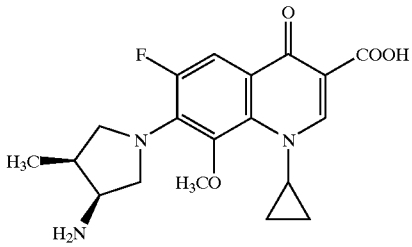

(VI)

DISCLOSURE OF INVENTION

The inventors of the present invention have carried out tests on the safety of the compound represented by the formula (VI) and found as the result that its mouse peripheral blood micronucleus test was positive (micronucleus inducing action).

The present inventors have conducted intensive studies with the aim of providing a compound which has excellent antibacterial activity, high efficacy and excellent safety in the clinical field. As the result, it has been found that an 8-methoxyquinoline compound substituted with 3-(S)-amino-4-(S)-fluoromethylpyrrolidin-1-yl group, represented by the following formula (I), is superior to its corresponding 8-methoxyquinoline compound substituted with 3-(S)-amino-4-(S)-methylpyrrolidin-1-yl group, represented by the aforementioned formula (VI), thereby resulting in the accomplishment of the present invention.

That is, it has been found that the compound represented by the following formula (I) is possessed of excellent antibacterial activity upon a broad range of Gram-negative and Gram-positive bacteria and have excellent safety and pharmacokinetics, such as its micronucleus test-negative property.

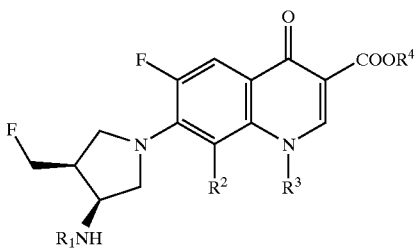

(I)

[In the above formula, $R^1$ represents a hydrogen atom or an alkyl group having 1 to 6 carbon atoms, wherein the alkyl group may have one or more substituent(s) selected from the group consisting of a hydroxyl group, a halogen atom, an alkylthio group having 1 to 6 carbon atoms and an alkoxyl group having 1 to 6 carbon atoms, $R^2$ represents a halogenomethoxyl group or an alkoxyl group having 1 to 6 carbon atoms, $R^3$ represents an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms which may have a substituent, a heteroaryl group which may have a substituent, an alkoxyl group having 1 to 6 carbon atoms or an alkylamino group having 1 to 6 carbon atoms, and $R^4$ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, 3-acetoxy-2-oxobutyl group, an alkyl group having 1 to 6 carbon atoms, an alkoxylmethyl group having 2 to 7 carbon atoms or a phenylalkyl group composed of an alkylene group having 1 to 6 carbon atoms and a phenyl group.

In this connection, the substituent $R^4$ may also be a boron-containing group represented by the following formula:

$$-B(Y^{11})Y^{12}$$

wherein $Y^{11}$ and $Y^{12}$, each independently represents a fluorine atom or an alkylcarbonyloxy group having 2 to 4 carbon atoms.]

Accordingly, the present invention relates to a compound represented by the aforementioned formula (I), its salts or hydrates thereof.

The present invention also relates to the aforementioned 8-methoxyquinolone-carboxylic acid derivative, its salts or hydrates thereof in which the compound of formula (I) is a stereochemically pure compound;

the aforementioned compound, its salts or hydrates thereof, wherein $R^1$ in the formula (I) is a hydrogen atom;

the aforementioned compound, its salts or hydrates thereof, wherein $R^2$ in the formula (I) is a methoxyl group; 7-[3-(S)-amino-4-(S)-fluoromethyl-1-pyrrolidinyl]-1-cyclopropyl-6-fluoro-1,4-dihydro-8-methoxy-4-oxoquinoline-3-carboxylic acid, its salts or hydrates thereof, wherein $R^3$ in the formula (I) is a cyclopropyl group;

the aforementioned compound, its salts or hydrates thereof, wherein $R^3$ in the formula (I) is a halogenocyclopropyl group;

the aforementioned compound, its salts or hydrates thereof, wherein $R^3$ in the formula (I) is a 1,2-cis-halogenocyclopropyl group;

the aforementioned compound, its salts or hydrates thereof, wherein $R^3$ in the formula (I) is a stereochemically pure substituent;

the aforementioned compound, its salts or hydrates thereof, wherein $R^3$ in the formula (I) is a (1R,2S)-2-halogenocyclopropyl group;

7-[3-(S)-amino-4-(S)-fluoromethyl-1-pyrrolidinyl]-6-fluoro-1-[2-(S)-fluoro-1-(R)-cyclopropyl]-1,4-dihydro-8-methoxy-4-oxoquinoline-3-carboxylic acid, its salts or hydrates thereof, wherein $R^3$ in the formula (I) is a (1R,2S)-2-fluorocyclopropyl group;

a medicament which comprises the aforementioned compound, a hydrate thereof, a salt of the compound or a hydrate of the salt as an active ingredient; and an antibacterial agent or antibacterial preparation which comprises the aforementioned compound, a hydrate thereof, a salt of the compound or a hydrate of the salt as an active ingredient.

The present invention also relates to a compound represented by the following formula (II), its salts or hydrates thereof:

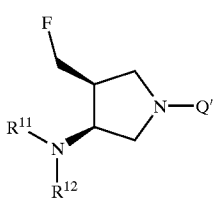

(II)

(wherein $R^{11}$ and $R^{12}$ each independently represents a hydrogen atom, an alkyl group having 1 to 6 carbon atoms or a protective group of the amino group, wherein the alkyl group may have one or more substituent (s) selected from the group consisting of a hydroxyl group, a halogen atom, an alkylthio group having 1 to 6 carbon atoms and an alkoxyl group having 1 to 6 carbon atoms, and Q' represents a protective group of the amino group or a hydrogen atom); and also relates to the aforementioned compound, its salts or hydrates thereof, wherein the protective group of the amino group is a protective group selected from the group consisting of (substituted) alkoxycarbonyl groups, (substituted) aralkyloxycarbonyl groups, (substituted) acyl groups, (substituted) alkyl groups, (substituted) aralkyl groups and (substituted) silyl groups;

the aforementioned compound, its salts or hydrates thereof, wherein the protective group of the amino group is a protective group selected from the group consisting of a tert-butoxycarbonyl group, a 2,2,2-trichloroethoxycarbonyl group, a benzyloxycarbonyl group, a para-methoxybenzyloxycarbonyl group, a para-nitrobenzyloxycarbonyl group, an acetyl group, a methoxyacetyl group, a trifluoroacetyl group, a chloroacetyl group, a pivaloyl group, a formyl group, a benzoyl group, a tert-butyl group, a benzyl group, a para-nitrobenzyl group, a para-methoxybenzyl group, a (R)-1-phenylethyl group, a (S)-1-phenylethyl group, a triphenylmethyl group, a methoxymethyl group, a tert-butoxymethyl group, a tetrahydropyranyl group, a 2,2,2-trichloroethoxymethyl group, a trimethylsilyl group, an isopropyldimethylsilyl group, a tert-butyldimethylsilyl group, a tribenzylsilyl group and a tert-butyldiphenylsilyl group;

the aforementioned compound, its salts or hydrates thereof, wherein one of $R^{11}$ and $R^{12}$ and Q' are protective groups of the amino group, which are different from each other;

3-(S)-tert-butoxycarbonylamino-4-(S)-fluoromethyl-1-(R)-phenylethylpyrrolidine, its salts or hydrates thereof;

3-(S)-tert-butoxycarbonylamino-4-(S)-fluoromethylpyrrolidine, its salts or hydrates thereof; and the aforementioned compound, its salts or hydrates thereof, wherein one of $R^{11}$ and $R^{12}$ and Q' are protective groups of the amino group, which are severed under different reaction conditions.

MODE FOR CARRYING OUT INVENTION

Each of the substituents of the compound of the present invention represented by formula (I):

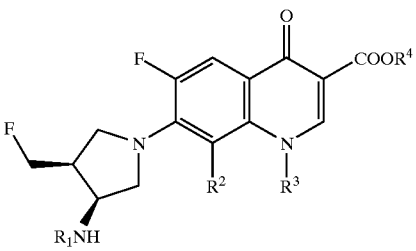

(I)

(wherein $R^1$, $R^2$, $R^3$ and $R^4$ are as defined in the foregoing) is described in the following.

The substituent $R^1$ is a hydrogen atom or an alkyl group having 1 to 6 carbon atoms, wherein the alkyl group may have one or more substituent(s) selected from the group consisting of a hydroxyl group, a halogen atom, an alkylthio group having 1 to 6 carbon atoms and an alkoxyl group having 1 to 6 carbon atoms.

The alkyl group may be any straight or branched group having 1 to 6 carbon atoms, and its preferred examples include a methyl group, an ethyl group, a normal propyl group and an isopropyl group.

When the alkyl group has a hydroxyl group as a substituent, the alkyl group may be either straight or branched form having 1 to 6 carbon atoms, and the substituting position of hydroxyl group may preferably be on the terminal carbon atom of the alkyl group. Preferred examples of the alkyl group having a hydroxyl group include those which have up to 3 carbon atoms, such as hydroxymethyl, 2-hydroxyethyl, 2-hydroxypropyl, 3-hydroxypropyl and the like groups.

When the alkyl group has a halogen atom as a substituent, the alkyl group may be either straight or branched form having 1 to 6 carbon atoms, and a fluorine atom is desirable as the halogen atom.

When the alkyl group has an alkylthio group as a substituent, the alkyl group may be either straight or branched form having 1 to 6 carbon atoms, and the alkylthio group may also be either straight or branched form having 1 to 6 carbon atoms. An alkylthiomethyl group, an alkylthioethyl group or an alkylthiopropyl group is desirable as the alkyl group having an alkylthio group, and the alkylthio group may preferably have up to 3 carbon atoms. Its more preferred examples include a methylthiomethyl group, an ethylthiomethyl group and a methylthioethyl group.

When the alkyl group has an alkoxyl group as a substituent, the alkyl group may be either straight or branched form having 1 to 6 carbon atoms, and the alkoxyl group may also be either straight or branched form having 1 to 6 carbon atoms. An alkoxymethyl group, an alkoxyethyl group or an alkoxypropyl group is desirable as the alkyl group having an alkoxyl group, and the alkoxyl group may preferably have up to 3 carbon atoms. Its more preferred examples include a methoxymethyl group, an ethoxymethyl group and a methoxyethyl group.

The substituent $R^2$ is a halogenomethoxyl group or an alkoxyl group having 1 to 6 carbon atoms.

As the halogen of the halogenomethoxyl group, a fluorine atom is particularly desirable, and its number may be from 1 to 3.

The alkoxyl group may be an alkoxyl group having 1 to 6 carbon atoms, preferably a methoxyl group and an ethoxyl group.

Among these substituents, a difluoromethoxyl group and a methoxyl group are preferred, and a methoxyl group is more preferred.

The substituent R³ is an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms which may have a substituent, a heteroaryl group which may have a substituent, an alkoxyl group having 1 to 6 carbon atoms, an alkylamino group having 1 to 6 carbon atoms or an aryl group which may have one or more substituent(s).

In this case, an ethyl group is desirable as the alkyl group having 1 to 6 carbon atoms. A vinyl or 1-isopropenyl group is desirable as the alkenyl group having 2 to 6 carbon atoms. A 2-fluoroethyl group is desirable as the halogenoalkyl group having 1 to 6 carbon atoms. A cyclopropyl or 2-halogenocyclopropyl group is desirable as the cyclic alkyl group having 3 to 6 carbon atoms which may have a substituent, and a fluorine atom is particularly desirable as the halogen atom of the 2-halogenocyclopropyl group.

Examples of the aryl group which may have one or more substituent(s) include phenyl or the like group which may have 1 to 3 substituents selected from the group consisting for example of fluorine, chlorine, bromine or the like halogen atom, a lower alkyl group having 1 to 6 carbon atoms, a hydroxyl group, an amino group, a nitro group and a lower alkoxyl group having 1 to 6 carbon atoms, and its preferred illustrative examples include a phenyl group, a 2-fluorophenyl group, a 4-fluorophenyl group, a 2,4-difluorophenyl group and a 2-fluoro-4-hydroxyphenyl group.

The heteroaryl group is a group derived from an aromatic heterocyclic compound which contains one or more heteroatoms selected from a nitrogen atom, an oxygen atom and a sulfur atom. Its examples include pyridyl, pyrimidyl and the like groups. As a substituent on these rings, an alkyl group, a halogen atom or the like is desirable. A methoxyl group is desirable as the alkoxyl group having 1 to 6 carbon atoms. A methylamino group is desirable as the alkylamino group having 1 to 6 carbon atoms.

As the substituent R³, a cyclic alkyl group or a halogenocycloalkyl group is desirable. Among these groups, a cyclopropyl group or a 2-halogenocyclopropyl group is particularly desirable. A fluorine atom is desirable as the halogen atom.

Next, the halogenocyclopropyl group of R³ is described.

As the substituting halogen atom, fluorine and chlorine can be exemplified, and fluorine is particularly preferred.

Stereochemical environment at this moiety with respect to the cyclopropane ring, it is particularly desirable that the halogen atom and the pyridonecarboxylic acid moiety are located in the cis-configuration.

So-called enantiomeric isomers exist solely by the cis-2-halogenocyclopropyl moiety of R³, and strong antibacterial activity and high safety have been observed in all of these isomers.

The present invention exerts excellent characteristics as the substituent represented by formula (VII):

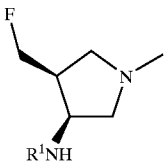

(VII)

is substituted at the 7-position of the 6-fluoro-1,4-dihydro-4-oxoquinoline-3-carboxylic acid nucleus.

The present invention is characterized in that the amino group at the 3-position and the fluoromethyl group at the 4-position on the pyrrolidine ring of this substituent are located in the cis-configuration and absolute configuration of (3S,4S)-form.

That is, it has been found that, when the substituent at the 7-position of the 6-fluoro-1,4-dihydro-4-oxoquinoline-3-carboxylic acid nucleus is 3-(S)-amino-4-(S)-fluoromethylpyrrolidin-1-yl group, the compound of the present invention shows potent antibacterial activity upon Gram-negative and Gram-positive bacteria and also shows excellent safety and good pharmacokinetics, such as negative property in micronucleus test, markedly weak theophylline metabolism inhibitory activity and the like.

When the compound of the formula (I) of the present invention has a structure in which diastereomers are present, and when such a compound of the present invention is administered to human and animals, it is desirable to administer a compound which comprises a single diastereomer. The term "single" of "comprises a single diastereomer" as used herein means not only a case in which it is completely free from the other diastereomer but also a case in which it is in a chemically pure degree. In other words, it is interpretable that the other diastereomer may be present in such a degree that it does not exert influences upon physical constants and physiological activities of the compound.

Also, the term "stereochemically pure" as used herein means that, when a compound or the like exists in a plurality of isomer forms due to the presence of asymmetric carbon atoms, the compound is comprised of only one of them. The term "pure" in this case can also be considered in the same manner as the term "single" described above.

The 6-fluoro-1,4-dihydro-4-oxoquinoline-3-carboxylic acid derivative of the present invention may be used either in its free form or as an acid addition salt or a salt of its carboxyl group. Examples of the acid addition salt include hydrochloride, sulfate, nitrate, hydrobromide, hydroiodide, phosphate and the like inorganic acid salts, or acetate, methanesulfonate, benzenesulfonate, toluenesulfonate, citrate, maleate, fumarate, lactate and the like organic acid salts.

The salt of carboxyl group may be either inorganic or organic salt, and its illustrative examples include lithium salt, sodium salt, potassium salt and the like alkali metal salts, magnesium salt, calcium salt and the like alkaline earth metal salts, ammonium salt, or triethylamine salt, N-methylglucamine salt, tris-(hydroxylmethyl) aminomethane salt and the like.

Also, these free form, acid addition salts and salts of carboxyl group of the 6-fluoro-1,4-dihydro-4-oxoquinoline-3-carboxylic acid derivative may be present as hydrates.

On the other hand, a quinolone derivative whose carboxylic acid moiety is an ester is useful as a synthesis intermediate or a prodrug. For example, alkyl esters, benzyl esters, alkoxyalkyl esters, phenylalkyl esters and phenyl esters are useful as synthesis intermediates.

Also, the ester to be used as a prodrug is an ester which is easily cleaved after administered to form free carboxylic acid, and its illustrative examples include acetoxymethyl ester, pivaloyloxymethyl ester, ethoxycarbonyl ester, choline ester, dimethylaminoethyl ester, 5-indanyl ester, phthalidinyl ester, and 5-alkyl-2-oxo-1,3-dioxol-4-ylmethyl ester, 3-acetoxy-2-oxobutyl eater or the like oxoalkyl ester.

The compound of the present invention represented by the formula (I) can be produced by various method, and, in an preferred example of these methods, it can be produced for example by allowing a compound represented by formula (VIII):

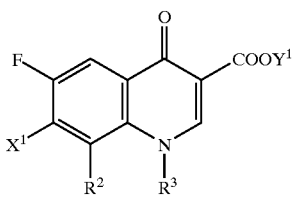

(VIII)

[wherein $X^1$ is a substituent which serves as a leaving group, such as a fluorine atom, a chlorine atom, substituted or unsubstituted phenylsulfonyl group or a substituted or unsubstituted alkylsulfonyl group having 1 to 3 carbon atoms, $Y^1$ is the $R^4$ defined in the formula (I) or a boron-containing group represented by the following formula:

(wherein each of $Y^{11}$ and $Y^{12}$ is a fluorine atom or an alkylcarbonyloxy group having 2 to 4 carbon atoms), and $R^2$ and $R^3$ are as defined in the formula (I)] to react with a compound represented by formula (IX):

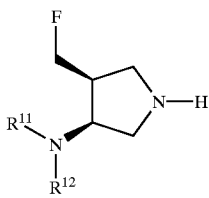

(IX)

(wherein $R^{11}$ and $R^{12}$, each independently represents a hydrogen atom, an alkyl group having 1 to 6 carbon atoms or a protective group of the amino group, wherein the alkyl group may have one or more substitutent(s) selected from the group consisting of a hydroxyl group, a halogen atom, an alkylthio group having 1 to 6 carbon atoms and an alkoxyl group having 1 to 6 carbon atoms, or an addition salt thereof (as the acid addition salt, an inorganic acid salt or an organic acid salt can be exemplified, and its illustrative examples include hydrochloride, sulfate, nitrate, hydrobromide, hydroiodide, phosphate and the like inorganic acid salts, or methanesulfonate, benzenesulfonate, toluenesulfonate (sulfonates), acetate, citrate, maleate, fumarate, lactate (carboxylates) and the like organic acid salts).

The reaction can be carried out using or without using a solvent. The solvent to be used in the reaction may be any solvent which is inert under the reaction conditions, and its illustrative examples include dimethyl sulfoxide, pyridine, acetonitrile, ethanol, chloroform, dimethylformamide, dimethylacetamide, N-methylpyrrolidone, tetrahydrofuran, water, 3-methoxybutanol and the like or a mixture thereof.

Preferably, the reaction may be carried out in the presence of an acid acceptor such as an inorganic base or an organic base, which includes an alkali metal or alkaline earth metal carbonate or bicarbonate or the like inorganic basic compound, or triethylamine, pyridine, 1,8-diazabicycloundecene or the like organic basic compound.

The reaction temperature may be within the range of generally from room temperature to 200° C., preferably from approximately 25 to 150° C. The reaction is carried out for a period of from 30 minutes to 48 hours and completes generally after about 30 minutes to 20 hours.

Examples of the protective group of the amino group to be used in the compound represented by the formula (IX) include those which are generally used in this field, such as tert-butoxycarbonyl, 2,2,2-trichloroethoxycarbonyl and the like (substituted) alkoxycarbonyl groups, benzyloxycarbonyl, para-methoxybenzyloxycarbonyl, para-nitrobenzyloxycarbonyl and the like (substituted) aralkyloxycarbonyl groups, acetyl, methoxyacetyl, trifluoroacetyl, chloroacetyl, pivaloyl, formyl, benzoyl and the like (substituted) acyl groups, tert-butyl, benzyl, para-nitrobenzyl, para-methoxybenzyl, triphenylmethyl and the like (substituted) alkyl groups or (substituted) aralkyl groups, methoxymethyl, tert-butoxymethyl, tetrahydropyranyl, 2,2,2-trichloroethoxymethyl and the like ethers and trimethylsilyl, isopropyldimethylsilyl, tert-butyldimethylsilyl, tribenzylsilyl, tert-butyldiphenylsilyl and the like substituted silyl groups (the term "(substituted)" as used herein means "which may have a substituent").

When $Y^1$ is an alkyl group having 1 to 6 carbon atoms, an alkoxymethyl group having 2 to 7 carbon atoms or a phenylalkyl group composed of an alkylene group having 1 to 6 carbon atoms and a phenyl group, the compound of interest can be converted into its corresponding carboxylic acid by treating it under an acidic or basic condition which is generally employed for the hydrolysis of carboxylic acid esters.

When $Y^1$ is a boron-containing group of the formula:

its conversion into corresponding carboxylic acid can be effected by allowing a compound represented by the formula (IX) to react with a compound of the formula (VIII) and then treating it under an acidic or basic condition.

In addition, when deprotection is necessary, the compound of interest represented by the formula (I) can be obtained by removing the protective group by selecting suitable conditions for the protective group.

The compound represented by the formula (VIII) can be produced by already known methods. Also, a compound in which $Y^1$ is a boron-containing group can be obtained by allowing the carboxylic acid or a ester derivative thereof to react with a boron fluoride compound or anhydrous boron carboxylate.

In the compound in which $Y^1$ is a boron-containing group, each of $Y^{11}$ and $Y^{12}$ is a fluorine atom or an acyloxy group. The acyloxy group may be either aliphatic (becomes an alkylcarbonyloxy group) or aromatic, and either may have an additional substituent. As such a substituent, it may have one or more substituent(s) selected from the group consisting of a halogen atom, an alkyl group having 1 to 6 carbon atoms and an alkoxyl group having 1 to 6 carbon atoms. Examples of the acyloxy group include acetyloxy, propanoyloxy, butanoyloxy, benzoyloxy, phenylacetyloxy and the like groups, of which an acyloxy group having 2 to 4 carbon atoms (an alkylcarbonyloxy group) is preferred and an acetyloxy group is particularly preferred.

The compound represented by the formula (IX) can be formed by removing Q' from the compound of formula (II):

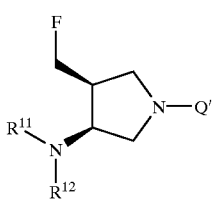

(II)

[wherein $R^{11}$ and $R^{12}$, each independently represents a hydrogen atom, an alkyl group having 1 to 6 carbon atoms or a protective group of the amino group, wherein the alkyl group may have one or more substituent(s) selected from the group consisting of a hydroxyl group, a halogen atom, an alkylthio group having 1 to 6 carbon atoms and an alkoxyl group having 1 to 6 carbon atoms, and Q' represents a protective group of the amino group or a hydrogen atom, and wherein the amino protective group may be a protective group selected from the group consisting of (substituted) alkoxycarbonyl groups, (substituted) aralkyloxycarbonyl groups, (substituted) acyl groups, (substituted) alkyl groups, (substituted) aralkyl groups and substituted silyl groups.]

The compound represented by the formula (IX) and the compound represented by the formula (II) can be produced by various method. For example, 3-(S)-tert-butoxycarbonylamino-4-(S)-fluoromethylpyrrolidine can be synthesized in accordance with the method described as a desirable method in Reference Examples, though not particularly limited.

The compound represented by the formula (II) can also exist in the form of a salt thereof, a hydrate thereof or a hydrate of the salt. Examples of its acid addition salt include an inorganic acid salt or an organic acid salt, and its illustrative examples include hydrochloride, sulfate, nitrate, hydrobromide, hydroiodide, phosphate and the like inorganic acid salts, or methanesulfonate, benzenesulfonate, toluenesulfonate (sulfonates), acetate, citrate, maleate, fumarate, lactate (carboxylates) and the like organic acid salts.

When one of $R^{11}$ and $R^{12}$ is a protective group of the amino group and Q' is also a protective group of the amino group, these groups may be the same or different from each other, but it is convenient to obtain a compound in which each of them is removed under different reaction condition, namely one of them is selectively removed but the other remains un-removed, for the production the compound (I).

The following can be exemplified as $R^{11}$ or $R^{12}$ (either one of them) and Q' which are the protective groups of the amino group. That is, they are (substituted) alkoxycarbonyl groups, (substituted) aralkyloxycarbonyl groups, (substituted) acyl groups, (substituted) alkyl groups, (substituted) aralkyl groups and substituted silyl groups.

Their illustrative examples include tert-butoxycarbonyl, 2,2,2-trichloroethoxycarbonyl and the like (substituted) alkoxycarbonyl groups, benzyloxycarbonyl, para-methoxybenzyloxycarbonyl, para-nitrobenzyloxycarbonyl and the like aralkyloxycarbonyl groups, acetyl, methoxyacetyl, trifluoroacetyl, chloroacetyl, pivaloyl, formyl, benzoyl and the like (substituted) acyl groups, tert-butyl, benzyl, para-nitrobenzyl, para-methoxybenzyl, triphenylmethyl and the like (substituted) alkyl groups or (substituted) aralkyl groups, methoxymethyl, tert-butoxymethyl, tetrahydropyranyl, 2,2,2-trichloroethoxymethyl and the like ethers and trimethylsilyl, isopropyldimethylsilyl, tert-butyldimethylsilyl, tribenzylsilyl, tert-butyldiphenylsilyl and the like substituted silyl groups.

Cis-2-fluorocyclopropylamine comprised of a single isomer which is desirable for the synthesis of the compound of the formula (I) comprised of a single isomer can, for example, be synthesized by the method described in JP-A-2-231475. Synthesis of the compound of the formula (I) comprised of a single isomer can, for example, be carried out in accordance with the method described in JP-A-2-231475, using the thus obtained optically active cis-2-fluorocyclopropylamine derivative as the material.

Since the compound of the present invention has potent antibacterial activities, it can be used as medicaments for use in human bodies, animals and fishes or as preservatives of agricultural chemicals and food.

When the compound of the present invention is used as a medicament for human bodies, its dosage may be within the range of generally from 50 mg to 1 g, preferably from 100 mg to 300 mg, per day per adult.

Its dosage as a drug for animals varies depending on the purpose of its administration (treatment or prevention), kind and size of each animal to be treated and kind and degree of each infected pathogenic bacterium, but the dosage may be within the range of generally from 1 mg to 200 mg, preferably from 5 mg to 100 mg, per 1 kg body weight per day.

The daily dose may be used once a day or by dividing it into 2 to 4 doses per day. As occasion demands, the daily dose may exceed the aforementioned range.

Since the compound of the present invention has activity against a broad range of microorganisms which cause various infectious diseases, it can treat, prevent or alleviate diseases induced by these pathogens.

Illustrative examples of bacteria or bacterioid microorganisms on which the compound of the present invention is effective include those which belong to the genus Staphylococcus, *Streptococcus pyogens*, hemolytic streptococcus, enterococcus, pneumococcus, those which belong to the genus Peptostreptococcus, *Neisseria gonorrhoeae, Escherichia coli*, those which belong to the genus Citrobacter, those which belong to the genus Shigella, *Klebsiella pneumoniae*, those which belong to the genus Enterobacter, those which belong to the genus Serratia, those which belong to the genus Proteus, *Pseudomonas aeruginosa, Haemophilus influenzae*, those which belong to the genus Acinetobacter, those which belong to the genus Campylobacter, *Chlamydia trachomatis* and the like.

Illustrative examples of diseases which are induced by these pathogens include folliculitis, furuncle, carbuncle, erysipelas, phlegmon, lymphangitis, felon, subcutaneous abscess, hidradenitis, acne conglobata, infectious atheroma, perirectal abscess, mastitis, superficial secondary infections after injury, burn injury, operative wound and the like, pharyngitis, acute bronchitis, tonsilitis, chronic bronchitis, bronchiectasis, diffuse bronchiolitis, secondary infection of chronic respiratory disease, pneumonia, pyelonephritis, cystitis, prostatitis, epididymitis, gonococcal urethritis, non-specific urethritis, cholecystitis, cholangitis, bacillary dysentery, enteritis, uterine adnexitis, intrauterine infection, bartholinitis, blepharitis, hordeolum, dacryocystitis, tarsadenitis, corneal ulcer, octitis media, sinusitis, periodentitis, pericoronitis, jaw infection, peritonitis, endocarditis, sepsis, meningitis, skin infection and the like.

The compound of the present invention is also effective against various microorganisms which cause infectious diseases in animals, such as those which belong to the genera Escherichia, Salmonella, Pasteurella, Haemophilus, Bordetella, Staphylococcus, Mycoplasma and the like.

Illustrative examples of such diseases include colibacillosis, pullorum disease, avian paratyphoid, avian cholera, infectious coryza, staphylococcosis, mycoplasma infection and the like in the case of birds; colibacillosis, salmonellosis, pasteurellosis, haemophilus infection, atrophic rhinitis, exudative epidermis, mycoplasma infection and the like in the case of pigs; colibacillosis, salmonellosis, hemorrhagic sepsis, mycoplasma infection, bovine pleuropneumonia, bovine mastitis and the like in the case of cattle; colisepsis, salmonella infection, hemorrhagic sepsis, uterine empyema, cystitis and the like in the case of dogs; and exudative pleurisy, cystitis, chronic rhinitis, haemophilus infection, kitten diarrhea, mycoplasma infection and the like in the case of cats.

The antibacterial preparation which comprises the compound of the present invention can be prepared by selecting appropriate preparation depending on each administration method and employing generally used various preparation method. With regard to the dosage forms of the antibacterial preparation which uses the compound of the present invention as its principal agent, tablets, powders, granules, capsules, solutions, syrups, elixirs, oily or aqueous suspensions and the like can be exemplified as oral preparations.

With regard to injections, a stabilizing agent, an antiseptic agent, a solubilizing agent and the like may be used in the preparation, and a solution which may contain these auxiliary agents may be contained in a container and made into a solid preparation by freeze-drying or the like means to be re-dissolved when used. In addition, a single dose may be contained in a single container or multiple doses may be contained in the same container.

Also, solutions, suspensions, emulsions, ointments, gels, creams, lotions, sprays and the like can be exemplified as preparations for external use.

Solid preparations may contain pharmaceutically acceptable additives together with the active compound and can be prepared for example by mixing the compound with additives optionally selected from fillers, extenders, binders, disintegrators, solubilization enhancing agents, moistening agents, lubricating agents and the like.

As liquid preparations, solutions, suspensions, emulsions and the like can be exemplified, which may contain a suspending agent, an emulsifying agent and the like as additives.

Examples of the method for administering the compound of the present invention to animals include a method in which it is orally administered directly or by mixing it with feed, a method in which it is made into a solution and then orally administered directly or by mixing it with drinking water or feed and a method in which it is administered by injection.

With regard to the pharmaceutical preparations for use in the administration of the compound of the present invention to animals, it can be made optionally into powders, fine subtilaes, soluble powders, syrups, solutions or injections making use of the techniques generally used in this field.

Formulation examples of the pharmaceutical preparations are shown below.

TABLE 1

Formulation Example 1 (Capsules):

| | |
|---|---|
| Compound of Inventive Example 2 | 100.0 mg |
| Corn starch | 23.0 mg |
| CMC calcium | 22.5 mg |

TABLE 1-continued

| | |
|---|---|
| Hydroxymethyl cellulose | 3.0 mg |
| Magnesium stearate | 1.5 mg |
| Total | 150.0 mg |
| Formulation Example 2 (Solutions): | |
| Compound of Inventive Example 2 | 1–10 g |
| Acetic acid or sodium hydroxide | 0.5–2 g |
| Ethyl para-hydroxybenzoate | 0.1 g |
| Purified water | 87.9–98.4 g |
| Total | 100 g |
| Formulation Example 3 (Powders for feed mixing use): | |
| Compound of Inventive Example 2 | 1–10 g |
| Corn starch | 98.5–89.5 g |
| Light anhydrous silicic acid | 0.5 g |
| Total | 100 g |

BEST MODE FOR CARRYING OUT INVENTION

Examples of the present invention are given below by way of illustration and not by way of limitation. The antibacterial activity of each compound of interest was measured in accordance with the standard method specified by the Japan Society of Chemotherapy, with the results shown in Table 1 as MIC values ($\mu$g/ml).

REFERENCE EXAMPLE 1

4-(S)-Fluoromethyl-N-[1-(R)-phenylethyl]-2-pyrrolidone

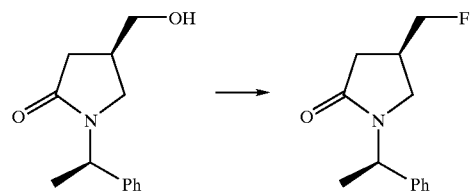

Method A

Diethylamino sulfur trifluoride (1.90 ml, 14.38 mmol) was added to a methylene chloride (50 ml) solution of 4-(S)-hydroxymethyl-N-[1-(R)-phenylethyl]-2-pyrrolidone (2.00 g, 9.12 mmol) at −78° C., and the mixture was stirred overnight while gradually warming to room temperature. The reaction solution was washed with saturated sodium bicarbonate aqueous solution and saturated brine in that order and then dried over anhydrous sodium sulfate. After evaporation of the solvent, the resulting residue was subjected to a silica gel chromatography to give 1.11 g (55%) of the title compound from the 3% methanol-chloroform eluate in the form of a light yellow oil.

Method B

Triethylamine (6.36 ml, 45.63 mmol) was added to a methylene chloride (100 ml) solution of 4-(S)-hydroxymethyl-N-[1-(R)-phenylethyl]-2-pyrrolidone (5.00 g, 22.80 mmol), methanesulfonyl chloride (2.65 ml, 34.24 mmol) was added dropwise to the thus prepared solution which was cooled in an ice bath and then the resulting mixture was stirred for 30 minutes at the same temperature.

The reaction solution was washed with 10% citric acid aqueous solution and dried over sodium sulfate, and the solvent was then evaporated. The thus obtained residue was dissolved in tetrahydrofuran (100 ml), mixed with 1N tetra-n-butylammonium fluoride-tetrahydrofuran solution (114 ml) and then heated under reflux for 1.5 hours. The reaction solution was mixed with 10% citric acid aqueous solution, tetrahydrofuran was evaporated, the thus obtained residue was extracted with chloroform (200 ml ×3) and then the resulting organic layers were combined and dried over sodium sulfate. The solvent was evaporated and the thus obtained residue was subjected to a silica gel chromatography to give the title compound from the eluate of ethyl acetate:hexane=3:1, quantitatively in the form of a light yellow oil.

$^1$H-NMR (CDCl$_3$) δ: 1.52 (3H, d, J=7.33 Hz), 2.24–2.29 (1H, m), 2.52–2.63 (2H, m), 3.10 (1H, t, J=9.76 Hz), 3.20 (1H, dd, J=5.37, 9.76 Hz), 4.26–4.47 (2H, m), 5.50 (1H, q, J=7.32 Hz), 7.26–7.36 (5H, m).

REFERENCE EXAMPLE 2

4-(S)-Fluoromethyl-3-(R)-hydroxy-N-[1-(R)-phenylethyl]-2-pyrrolidone

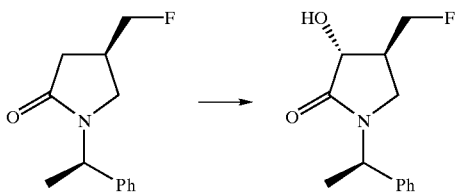

In an atmosphere of nitrogen and at −78° C., 1.66 N n-butyllithium-hexane solution (7.08 ml) was added dropwise to a tetrahydrofuran (20 ml) solution of diisopropylamine (1.65 ml, 11.75 mmol), and the mixture was stirred at 0° C. for 5 minutes. The reaction solution was cooled to −78° C. and added dropwise to a tetrahydrofuran (20 ml) solution of 4-(S)-fluoromethyl-N-[1-(R)-phenylethyl]-2-pyrrolidone (2.00 g, 9.04 mmol) at −78° C. in an atmosphere of nitrogen. After 15 minutes of stirring at the same temperature, degassing was effected under a reduced pressure, the atmosphere in the reaction container was replaced with oxygen gas and then the reaction mixture was stirred at the same temperature in an atmosphere of oxygen. After completion of the reaction, the reaction solution was mixed with 5% sodium thiosulfate aqueous solution, tetrahydrofuran was evaporated, the thus obtained residue was extracted with ethyl acetate (150 ml×3) and then the resulting organic layers were combined and dried over sodium sulfate. The solvent was evaporated and the thus obtained residue was subjected to a silica gel chromatography to give 1.57 g (73%) of the title compound from the eluate of 3% methanol-chloroform in the form of white crystals.

$^1$H-NMR (CDCl$_3$) δ: 1.52 (3H, d, J=7.32 Hz), 2.31–2.48 (1H, m), 3.05–3.10 (1H, m), 3.16–3.21 (1H, m), 4.29 (1H, d, J=9.37 Hz), 4.53–4.67 (2H, m), 5.48 (1H, q, J=7.33 Hz), 7.26–7.37 (5H, m).

REFERENCE EXAMPLE 3

3-(S)-Azido-4-(S)-fluoromethyl-N-[1-(R)-phenylethyl]-2-pyrrolidone

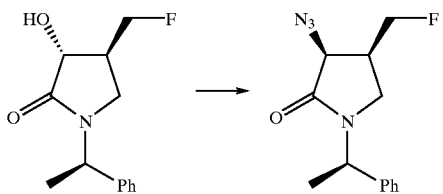

Triethylamine (3.07 ml, 22.02 mmol) was added to a methylene chloride (40 ml) solution of 4-(S)-fluoromethyl-3-(R)-hydroxy-N-[1-(R)-phenylethyl]-2-pyrrolidone (2.61 g, 11.00 mmol), methanesulfonyl chloride (1.28 ml, 16.54 mmol) was added dropwise to the thus prepared solution at −10° C. and then the resulting mixture was stirred for 30 minutes at the same temperature. The reaction solution was washed with 10% citric acid aqueous solution and dried over sodium sulfate and then the solvent was evaporated. The thus obtained residue was dissolved in N,N-dimethylformamide (80 ml), mixed with sodium azide (2.86 g, 44.00 mmol) and then stirred overnight at 100° C. The reaction solution was mixed with water, extracted with ethyl acetate (200 ml×3) and then the resulting organic layers were combined and dried over sodium sulfate, subsequently evaporating the solvent. The thus obtained residue was subjected to a silica gel chromatography to give 1.81 g (63%) of the title compound from the eluate of ethyl acetate:hexane=1:3 in the form of a light yellow oil.

$^1$H-NMR (CDCl$_3$) δ: 1.56 (3H, d, J=7.32 Hz), 2.67–2.75 (1H, m), 3.02 (1H, dd, J=7.32, 10.25 Hz), 3.23 (1H, dd, J=4.39, 10.25 Hz), 4.27 (1H, d, J=8.30 Hz), 4.38 (1H, ddd, J=7.81, 9.28, 46.39 Hz), 4.59 (1H, ddd, J=5.86, 9.28, 46.37 Hz), 5.48 (1H, q, J=7.32 Hz), 7.26–7.37 (5H, m).

REFERENCE EXAMPLE 4

3-(S)-tert-Butoxycarbonylamino-4-(S)-fluoromethyl-N-[1-(R)-phenylethyl]-2-pyrrolidone

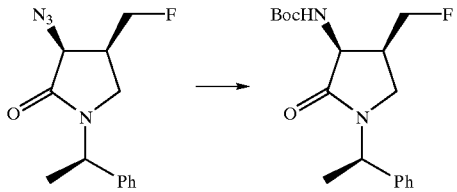

Di-tert-butyl dicarbonate (3.01 g, 13.79 mmol) and 10% palladium on carbon catalyst (1.80 g) were added to an ethanol (100 ml) solution of 3-(S)-azido-4-(S)-fluoromethyl-N-[1-(R)-phenylethyl]-2-pyrrolidone (1.81 g, 6.90 mmol), and the mixture was subjected to overnight catalytic hydrogenation at room temperature. After removal of the catalyst by filtration, the solvent of the resulting filtrate was evaporated, and the thus obtained residue was subjected to a silica gel chromatography. From the eluate of ethyl acetate:hexane=1:2, 1.68 g (72%) of the title compound was obtained as white crystals.

$^1$H-NMR (CDCl$_3$) δ: 1.45 (9H, s), 1.53 (3H, d, J=7.32 Hz), 2.85–2.93 (1H, m), 3.06 (1H, dd, J=6.25, 10.74 Hz), 3.31 (1H, d, J=9.26 Hz), 4.32–4.53 (3H, m), 5.08 (1H, brs), 5.49 (1H, q, J=6.83 Hz), 7.26–7.36 (5H, m).

REFERENCE EXAMPLE 5

3-(S)-tert-Butoxycarbonylamino-4-(S)-fluoromethyl-
N-[1-(R)-phenylethyl]-2-pyrrolidine

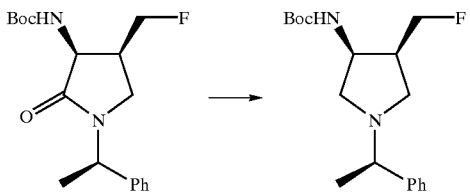

While cooling in an ice bath, a 1 mol tetrahydrofuran solution (19.98 ml) of borane-tetrahydrofuran complex was added dropwise to a tetrahydrofuran (60 ml) solution of 3-(S)-tert-butoxycarbonylamino-4-(S)-fluoromethyl-N-[1-(R)-phenylethyl]-2-pyrrolidone (1.68 g, 4.99 mmol), and the resulting mixture was stirred overnight at room temperature. The solvent was evaporated, and the thus obtained residue was mixed with an ethanol-water (4:1) mixed solvent (40 ml) and heated under reflux for 2 hours in the presence of triethylamine (8 ml). After spontaneous cooling, the solvent was evaporated. The thus obtained residue was mixed with chloroform and washed with saturated brine, the resulting organic layer was dried over sodium sulfate and then the solvent was evaporated. The resulting residue was subjected to a silica gel chromatography to give 1.54 g (96%) of the title compound from the eluate of ethyl acetate:hexane=1:3 in the form of white crystals.

$^1$H-NMR (CDCl$_3$) δ: 1.35 (3H, d, J=6.84 Hz), 1.43 (9H, s), 2.38–2.78 (5H, m), 3.24 (1H, q, J=6.34 Hz), 4.37–4.57 (3H, m), 4.84 (1H, d, J=8.30 Hz), 7.25–7.35 (5H, m).

REFERENCE EXAMPLE 6

3-(S)-tert-Butoxycarbonylamino-4-(S)-fluoromethylpyrrodine

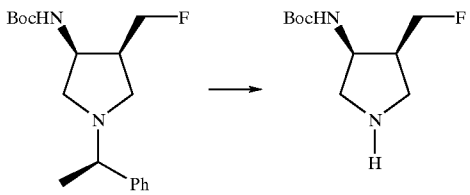

10% Palladium on carbon catalyst (500 mg) was added to an ethanol (50 ml) solution of 3-(S)-tert-butoxycarbonylamino-4-(S)-fluoromethyl-N-[1-(R)-phenylethyl]-pyrrolidine (484 mg, 1.50 mmol), and the mixture was subjected to overnight catalytic dehydrogenation at 50° C. After removing the catalyst by filtration, the solvent in the resulting filtrate was evaporated to give crude product of the title compound quantitatively.

$^1$H-NMR (CDCl$_3$) δ: 1.44 (9H, s), 1.69 (1H, brs), 2.45–2.53 (1H, m), 2.66 (1H, dd, J=5.37, 10.74 Hz), 2.90–2.95 (1H, m), 3.18 (2H, dd, J=7.81, 10.74 Hz), 4.18–4.27 (1H, m), 4.44–4.53 (1H, m), 4.56–4.65 (1H, m).

INVENTIVE EXAMPLE 1

7-[3-(S)-Amino-4-(S)-fluoromethyl-1-pyrrolidinyl]-
6-fluoro-1-[2-(S)-fluoro-1-(R)-cyclopropyl]-1,4-
dihydro-8-methoxy-4-oxoquinoline-3-carboxylic
acid

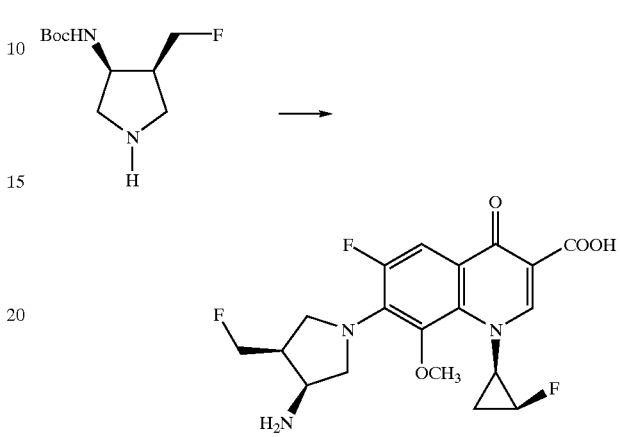

To a dimethyl sulfoxide (4 ml) solution of 6,7-difluoro-1-[2-(S)-fluoro-1-(R)-cyclopropyl]-1,4-dihydro-8-methoxy-4-oxoquinoline-3-carboxylic acid BF$_2$ complex (360 mg, 1.0 mmol) were added 3-(S)-tert-butoxycarbonylamino-4-(S)-fluoromethylpyrrolidine (218 mg, 1.00 mmol) and triethylamine (400 μl), subsequently carrying out 1 day of stirring at room temperature. Triethylamine was evaporated, the resulting residue was mixed with 10% citric acid aqueous solution and then the thus precipitated material was collected by filtration and washed with water. This was dissolved in 80% water-containing ethanol (50 ml), mixed with triethylamine (5 ml) and then heated overnight under reflux. The solvent was evaporated, and the thus obtained residue was mixed with concentrated hydrochloric acid and stirred at room temperature for 15 minutes. The reaction solution was washed with chloroform and then, while cooling in an ice bath, alkalified with 50% sodium hydroxide aqueous solution. This was adjusted to pH 7.4 with concentrated hydrochloric acid, and the aqueous layer was extracted with chloroform (300 ml×3). The organic layer was dried over sodium sulfate, the solvent was evaporated and then the resulting residue was recrystallized from 28% aqueous ammonia-ethanol to give 286 mg (70%) of the title compound in the form of light yellow crystals.

$^1$H-NMR (0.1N NaOD) δ: 1.41–1.62 (2H, m), 2.62–2.79 (1H, m), 3.44–3.47 (1H, m), 3.57 (3H, s), 3.60–3.65 (1H, m), 3.70–3.73 (1H, m), 3.77–3.88 (2H, m), 4.00–4.05 (1H, m), 4.55–5.08 (3H, m), 7.66 (1H, d, J=14.16 Hz), 8.42 (1H, d, J=2.44 Hz).

Elemental analysis data for C$_{19}$H$_{20}$F$_3$N$_3$O$_4$·0.25H$_2$O: Calcd.: C, 54.87; H, 4.97; N, 10.10 Found : C, 54.78; H, 4.83; N, 10.00 Melting point: 232–238° C. (decomp.) Specific rotation: [α]$_D$=−13.22° (c=0.174, 0.1 N sodium hydroxide solution)

INVENTIVE EXAMPLE 2

7-[3-(S)-Amino-4-(S)-fluoromethyl-1-pyrrolidinyl]-1-cyclopropyl-6-fluoro-1,4-dihydro-8-methoxy-4-oxoquinoline-3-carboxylic acid

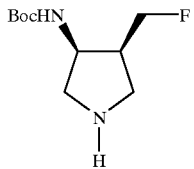
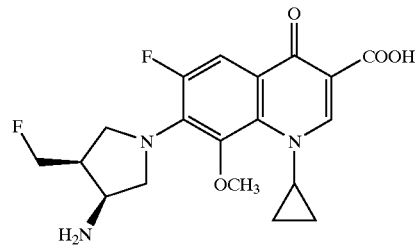

To a dimethyl sulfoxide (2 ml) solution of 1-cyclopropyl-6,7-difluoro-1,4-dihydro-8-methoxy-4-oxoquinoline-3carboxylic acid $EF_2$ complex (345 mg, 1.00 mmol) were added 3-(S)-tert-butoxycarbonylamino-4-(S)-fluoromethylpyrrolidine (327 mg, 1.00 mmol) and triethylamine (400 µl), subsequently carrying out 1 day of stirring at room temperature. Triethylamine was evaporated, the resulting residue was mixed with 10% citric acid aqueous solution and then the thus precipitated material was collected by filtration and washed with water. This was dissolved in 80% water-containing ethanol (50 ml), mixed with triethylamine (5 ml) and then heated overnight under reflux. The solvent was evaporated, and the thus obtained residue was mixed with concentrated hydrochloric acid and stirred at room temperature for 15 minutes. The reaction solution was washed with chloroform and then, while cooling in an ice bath, alkalified with 50% sodium hydroxide aqueous solution. This was adjusted to pH 7.4 with concentrated hydrochloric acid, and the aqueous layer was extracted with chloroform (300 ml×3). The organic layer was dried over sodium sulfate, the solvent was evaporated, and the resulting residue was isolated and purified by a preparative TLC through its development with a lower layer of chloroform:methanol:water=7:3:1 and then recrystallized from 28% aqueous ammonia-ethanol to give 185 mg (47%) of the title compound in the form of light yellow crystals.

$^1$H-NMR (0.1N NaOD) δ: 0.90–1.20 (4H, m), 2.73–2.78 (1H, m), 3.41–3.44 (1H, m), 3.58 (3H, s), 3.64–3.73 (3H, m), 3.90–3.96 (1H, m), 4.03–4.09 (1H, m), 4.66–4.82 (1H, m), 7.65 (1H, d, J=14.65 Hz), 8.49 (1H, s).

Elemental analysis data for $C_{19}H_{21}F_2N_3O_4 \cdot 0.25H_2O$: Calcd.: C, 57.35; H, 5.45; N, 10.56 Found : C, 57.36; H, 5.46; N, 10.41 Melting point: 204–207° C. (decomp.) Specific rotation: $[\alpha]_D = -92.00°$ (c=0.275, 0.1 N sodium hydroxide solution)

REFERENCE EXAMPLE 7

3-(S)-tert-Butoxycarbonylamino-4-(S)-fluoromethylpyrrolidine

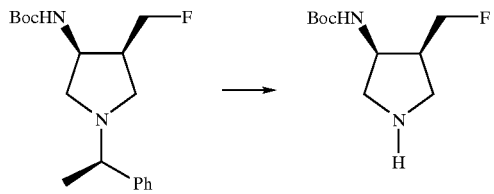

10% Palladium on carbon catalyst (640 mg) was added to an ethanol (15 ml) solution of 3-(S)-tert-butoxycarbonylamino-4-(S)-fluoromethyl-N-[1-(R)-phenylethyl]pyrrolidine (644 mg, 2.00 mmol), and the mixture was subjected to 2 hours of catalytic hydrogenation at 50° C. After removal of the catalyst by filtration, the solvent in the resulting filtrate was evaporated, and the thus obtained residue was mixed with 10% citric acid aqueous solution and washed with dichloromethane (15 ml×3) and diethyl ether (15 ml×1). The aqueous layer was adjusted to pH 10 to 11 with 1N sodium hydroxide aqueous solution and then extracted with chloroform (50 ml×4). The organic layer was dried over sodium sulfate, the solvent was evaporated and then the resulting residue was purified by recrystallizing it from a chloroform-n-hexane mixed solvent to give 344 mg (79%) of the title compound in the form of white crystals.

$^1$H-NMR (CDCl$_3$) δ: 1.45 (9H, s), 2.43–2.54 (1H, m), 2.67–2.70 (1H, m), 2.92–3.00 (1H, m), 3.18–3.25 (2H, m), 4.28 (1H, br.s.), 4.49 (1H, ddd, J=23.93, 9.28, 4.40 Hz), 4.61 (1H, ddd, J=23.93, 9.77, 4.40 Hz), 4.89 (1H, br.s.). IR (KBr disk) cm$^{-1}$: 3365, 3213, 2974, 2937, 2902, 2875, 1682, 1525, 1458, 1444, 1392, 1369, 1336, 1300, 1288, 1281, 1248. Elemental analysis data for $C_{10}H_{19}FN_2O_2 \cdot 0.25H_2O$: Calcd.: C, 53.92; H, 8.82; N, 12.57 Found : C, 54.25; H, 8.74; N, 12.74 Melting point: 78.0–79.3° C. Specific rotation: $[\alpha]_D = +28.60°$ (c=1.035, chloroform)

INVENTIVE EXAMPLE 3

7-[3-(S)-Amino-4-(S)-fluoromethyl-1-pyrrolidinyl]-6-fluoro-1-[2-(S)-fluoro-1-(R)-cyclopropyl]-1,4-dihydro-8-methoxy-4-oxoquinoline-3-carboxylic acid

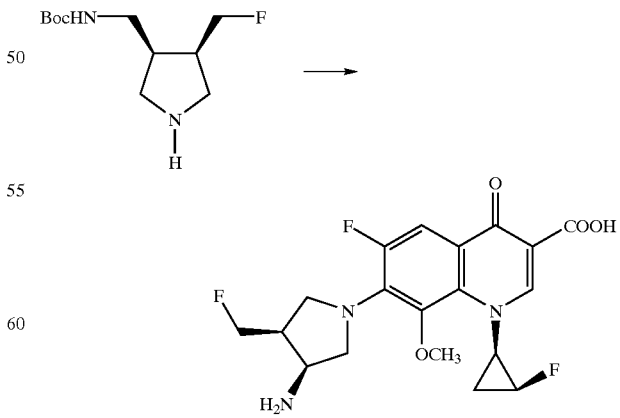

To a dimethyl sulfoxide (4 ml) solution of 6,7-difluoro-1-[2-(S)-fluoro-1-(R)cyclopropyl]-1,4-dihydro-8-methoxy- 4-oxoquinoline-3-carboxylic acid difluoroborane complex (360 mg, 1.00 mmol) were added 3-(S)-tert-butoxycarbonylamino-4-(S)-fluoromethylpyrrolidine (218 mg, 1.00 mmol) and triethylamine (400 μl), subsequently carrying out 1 day of stirring at room temperature. The reaction solution was concentrated under a reduced pressure, the thus concentrated solution was mixed with 10% citric acid aqueous solution, and the thus precipitated material was collected by filtration, washed with water, dissolved in a mixed solvent of ethanol:water=4:1 (50 ml), mixed with triethylamine (5 ml) and then heated overnight under reflux. The solvent was evaporated, and the thus obtained residue was mixed with concentrated hydrochloric acid and stirred at room temperature for 15 minutes. The reaction solution was washed with chloroform and then, while cooling in an ice bath, the aqueous layer was alkalified with 50% sodium hydroxide aqueous solution. This was adjusted to pH 7.4 with concentrated hydrochloric acid and 1N hydrochloric acid, and the aqueous layer was extracted with chloroform (300 ml×3). The organic layer was dried over sodium sulfate, the solvent was evaporated, and the resulting residue was recrystallized from 28% aqueous ammonia-ethanol to give 286 mg (70%) of the title compound in the form of light yellow crystals.

$^1$H-NMR (0.1N NaOD) δ: 1.41–1.62 (2H, m), 2.62–2.79 (1H, m), 3.44–3.47 (1H, m), 3.57 (3H, s), 3.60–3.65 (1H, m), 3.70–3.73 (1H, m), 3.77–3.88 (2H, m), 4.00–4.05 (1H, m), 4.55–5.08 (3H, m), 7.66 (1H, d, J=14.16 Hz), 8.42 (1H, d, J=2.44 Hz). Elemental analysis data for $C_{19}H_{20}F_3N_3O_4 \cdot 0.25H_2O$: Calcd.: C, 54.87; H, 4.97; N, 10.10 Found : C, 54.78; H, 4.83; N, 10.00 Melting point: 232–238° C. (decomp.) Specific rotation: $[\alpha]_D = -13.22°$ (c=0.174, 0.1 N sodium hydroxide solution)

INVENTIVE EXAMPLE 4

7-[3-(S)-Amino-4-(S)-fluoromethyl-1-pyrrolidinyl]-1-cyclopropyl-6-fluoro-1,4-dihydro-8-methoxy-4-oxoquinoline-3carboxylic acid

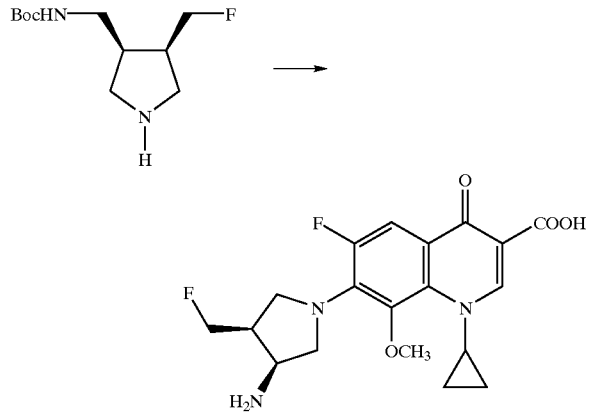

To a dimethyl sulfoxide (2 ml) solution of 1-cyclopropyl-6,7-difluoro-1,4-dihydro-8-methoxy-4-oxoquinoline-3-carboxylic acid difluoroborane complex (345 mg, 1.00 mmol) were added 3-(S)-tert-butoxycarbonylamino-4-(S)-fluoromethylpyrrolidine (327 mg, 1.00 mmol) and triethylamine (400 μl), subsequently carrying out 1 day of stirring at room temperature. The reaction solution was concentrated under a reduced pressure, the thus concentrated solution was mixed with 10% citric acid aqueous solution, and the thus precipitated material was collected by filtration, washed with water, dissolved in a mixed solvent of ethanol:water=4:1 (50 ml), mixed with triethylamine (5 ml) and then heated overnight under reflux. The solvent was evaporated, and the thus obtained residue was mixed with concentrated hydrochloric acid and stirred at room temperature for 15 minutes. The thus treated residue was washed with chloroform and then, while cooling in an ice bath, the aqueous layer was alkalified with 50% sodium hydroxide aqueous solution. This was adjusted to pH 7.4 with concentrated hydrochloric acid and 1N hydrochloric acid, and the aqueous layer was extracted with chloroform (300 ml×3). The organic layer was dried over sodium sulfate, the solvent was evaporated, and the resulting residue was isolated and purified by a preparative TLC through its development with a lower layer of chloroform:methanol:water=7:3:1 and then recrystallized from 28% aqueous ammonia-ethanol to give 185 mg (47%) of the title compound in the form of light yellow crystals.

$^1$H-NMR (0.1N NaOD) δ: 0.90–1.20 (4H, m), 2.73–2.78 (1H, m), 3.41–3.44 (1H, m), 3.58 (3H, s), 3.64–3.73 (3H, m), 3.90–3.96 (1H, m), 4.03–4.09 (1H, m), 4.66–4.82 (1H, m), 7.65 (1H, d, J=14.65 Hz), 8.49 (1H, s).

Elemental analysis data for $C_{19}H_{21}F_2N_3O_4 \cdot 0.25H_2O$: Calcd.: C, 57.35; H, 5.45; N, 10.56 Found : C, 57.36; H, 5.46; N, 10.41 Melting point: 204–207° C. (decomp.) Specific rotation: $[\alpha]_D = -92.00°$ (c=0.275, 0.1 N sodium hydroxide solution)

COMPARATIVE EXAMPLE 1

7-[3-(R)-Amino-4-(R)-fluoromethyl-1-pyrrolidinyl]-1-cyclopropyl-6-fluoro-1,4-dihydro-8-methoxy-4-oxoquinoline-3-carboxylic acid

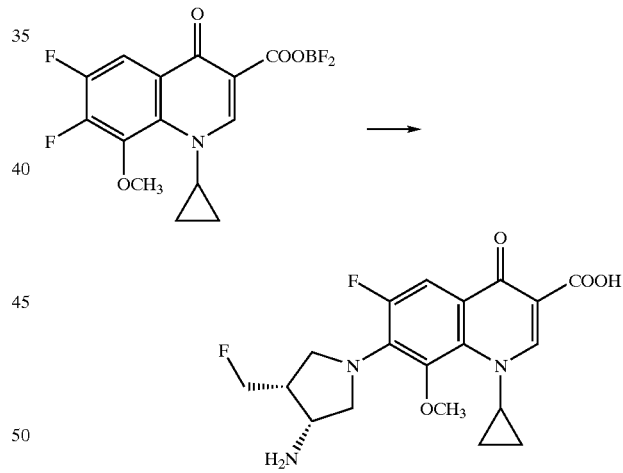

To a dimethyl sulfoxide (2 ml) solution of 1-cyclopropyl-6,7-difluoro-1,4-dihydro-8-methoxy-4-oxoquinoline-3-carboxylic acid difluoroborane complex (507 mg, 1.48 mmol) were added 3-(R)-tert-butoxycarbonylamino-4-(R)-fluoromethylpyrrolidine (419 mg, 1.92 mmol) that has been synthesized in accordance with the procedures described in Reference Examples 1 to 6 using 4-(R)-hydroxymethyl-N-[1-(R)-phenylethyl]-2-pyrrolidone which is a diastereomer of the starting material described in Reference Example 1, and triethylamine (454 μl), subsequently carrying out 38 hours of stirring at room temperature. The reaction solution was concentrated under a reduced pressure, the resulting residue was mixed with water (20 ml) and then the thus precipitated crystals were collected by filtration and washed with water. This was dissolved in a mixed solvent (30 ml) of ethanol:water=9:1, mixed with triethylamine (2 ml) and then heated under reflux for 4 hours. The solvent was evaporated, and the thus obtained residue was mixed with 10% citric acid aqueous solution (50 ml) and extracted with chloroform (100 ml×3). The organic layer was dried over sodium sulfate and the solvent was then evaporated. The thus obtained residue was dissolved in concentrated hydrochloric acid (10 ml) and washed with dichloromethane (50 ml×3) and then, while cooling in an ice bath, the aqueous layer was alkalified with 10 N sodium hydroxide aqueous solution. This aqueous layer was washed with dichloromethane (50 ml×3), adjusted to pH 7.4 with concentrated hydrochloric acid and 1N hydrochloric acid and then extracted with chloroform (100 ml×3). The organic layer was dried over sodium sulfate, the solvent was evaporated, and the resulting residue was purified by recrystallizing it from 28% aqueous ammonia-ethanol mixed solvent to give 472 mg (81%) of the title compound in the form of light yellow crystals.

$^1$H-NMR (0.1N NaOD) δ: 0.82—1.19 (4H, m), 2.65–2.75 (1H, m), 3.38 (1H, d, J=10.75 Hz), 3.51 (3H, s), 3.59–3.70 (3H, m), 3.84–3.88 (1H, m), 4.00–4.06 (1H, m), 4.64–4.86 (2H, m), 7.61 (1H, d, J=14.65 Hz), 8.49 (1H, s). IR (KBr disk) cm$^{-1}$: 3359, 3086, 2952, 2881, 1724, 1620, 1510, 1446, 1436, 1373, 1352, 1327, 1315, 1267, 1219. Elemental analysis data for $C_{19}H_{21}F_2N_3O_4$: Calcd.: C, 58.01; H, 5.38; N, 10.68 Found : C, 57.73; H, 5.40; N, 10.67 Melting point: 206.1–208.2° C. Specific rotation: $[α]_D$=+95.21° (c=1.065, 0.1 N NaOH solution)

INVENTIVE EXAMPLE 5

7-[3-(S)-tert-Butoxycarbonylamino-4-(S)-fluoromethyl-1-pyrrolidinyl]-1-cyclopropyl-6-fluoro-1,4-dihydro-8-methoxy-4-oxoquinoline-3-carboxylic acid difluoroborane complex

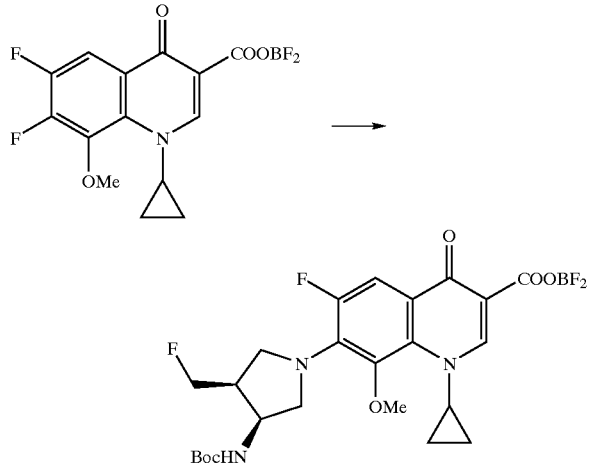

To a dimethyl sulfoxide (2 ml) solution of 1-cyclopropyl-6,7-difluoro-1,4-dihydro-8-methoxy-4-oxoquinoline-3-carboxylic acid difluoroborane complex (343 mg, 1.00 mmol) were added 3-(S)-tert-butoxycarbonylamino-4-(S)-fluoromethylpyrrolidine (284 mg, 1.30 mmol) and triethylamine (307 μl), subsequently carrying out 21 hours of stirring at room temperature. The reaction solution was concentrated under a reduced pressure, the thus concentrated solution was mixed with water (50 ml) and then the thus precipitated crystals were washed with water and diethyl ether. These crystals were purified by recrystallizing them from ethanol to give 285 mg (53%) of the title compound in the form of light yellow crystals.

$^1$H-NMR (CDCl$_3$) δ: 1.14–1.21 (2H, m), 1.33–1.36 (2H, m), 1.47 (9H, s), 2.78–2.84 (1H, m), 3.64 (4H, s), 3.87–3.90 (1H, m), 4.02–4.07 (1H, m), 4.29–4.31 (1H, m), 4.55 (1H, br.s), 4.61–4.83 (2H, m), 5.00 (1H, br.s), 7.84 (1H, d, J=13.67 Hz), 8.97 (1H, s). IR (KBr disk) cm$^{-1}$: 3423, 2981, 1716, 1631, 1568, 1524, 1502, 1443, 1410, 1394, 1367, 1338, 1286, 1254. Elemental analysis data for $C_{24}H_{28}BF_4N_3O_6 \cdot 0.75H_2O$: Calcd.: C, 51.96; H, 5.36; N, 7.57 Found : C, 52.07; H, 5.27; N, 7.57 Melting point: 154.3–155.2° C. (decomp.) Specific rotation: $[α]_D$=−1.03° (c=0.968, chloroform)

INVENTIVE EXAMPLE 6

7-[3-(S)-tert-Butoxycarbonylamino-4-(S)-fluoromethyl-1-pyrrolidinyl]-1-cyclopropyl-6-fluoro-1,4-dihydro-8-methoxy-4-oxoquinoline-3-carboxylic acid

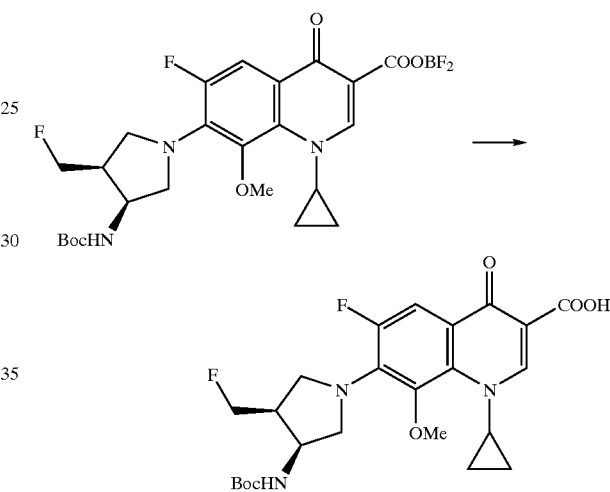

7-[3-(S)-tert-Butoxycarbonylamino-4-(S)-fluoromethyl-1-pyrrolidinyl]-1-cyclopropyl-6-fluoro-1,4-dihydro-8-methoxy-4-oxoquinoline-3-carboxylic acid difluoroborane complex (244 mg, 440 μmol) was dissolved in a mixed solvent (20 ml) of ethanol:water=4:1 and mixed with triethylamine (2 ml), and the mixture was heated under reflux for 4 hours. The solvent was evaporated, and the resulting residue was mixed with 10% citric acid aqueous solution (50 ml) and extracted with chloroform (100 ml×3). The organic layer was dried over sodium sulfate and the solvent was evaporated to give 256 mg of crude product of the title compound which was then purified by its recrystallization from a chloroform-n-hexane mixed solvent to give 194 mg (87%) of the title compound in the form of light yellow crystals.

$^1$H-NMR (0.1N NaOD) δ: 0.68–1.05 (4H, m), 1.30 (9H, s), 2.70–2.80 (1H, m), 3.34 (1H, d, J=10.26 Hz), 3.44 (3H, s), 3.52 (1H, t, J=8.30 Hz), 3.62 (1H, t, J=8.30 Hz), 3.83–3.85 (1H, m), 3.90–3.95 (1H, m), 4.27 (1H, br.s), 4.43–4.62 (2H, m), 7.51 (1H, d, J=14.16 Hz), 8.34 (1H, s). IR (KBr disk) cm$^{-1}$: 3359, 3086, 2976, 2935, 2881, 1716, 1624, 1512, 1450, 1392, 1369, 1313, 1273, 1248. Elemental analysis data for $C_{24}H_{29}F_2N_3O_6 \cdot 0.5H_2O$: Calcd.: C, 57.36; H, 6.02; N, 8.36 Found : C, 57.40; H, 5.97; N, 8.21 Melting point: 111.0–113.7° C. Specific rotation: $[α]_D$=−21.17° (c=0.992, chloroform)

INVENTIVE EXAMPLE 7

7-[3-(S)-Amino-4-(S)-fluoromethyl-1-pyrrolidinyl]-1-cyclopropyl-6-fluoro-1,4-dihydro-8-methoxy-4-oxoquinoline-3-carboxylic acid

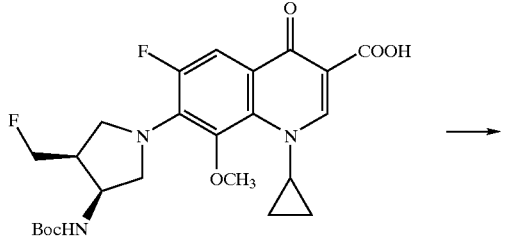

Concentrated hydrochloric acid (2 ml) was added to 7-[3-(S)-tert-butoxycarbonylamino-4-(S)-fluoromethyl-1-pyrrolidinyl]-1-cyclopropyl-6-fluoro-1,4-dihydro-8-methoxy-4-oxoquinoline -3-carboxylic acid (140 mg, 0.28 mmol) which was cooled in an ice bath, and the mixture was stirred for 30 minutes at the same temperature. The reaction solution was diluted with water (50 ml) and washed with chloroform (50 ml×3) and then, while cooling in an ice bath, the aqueous layer was alkalified with 50% sodium hydroxide aqueous solution. The aqueous layer was washed with dichloromethane (50 ml×3), adjusted to pH 7.4 with concentrated hydrochloric acid and 1N hydrochloric acid and then extracted with chloroform (100 ml×3). The organic layer was dried over sodium sulfate, the solvent was evaporated, and the thus obtained residue was purified by its recrystallization from a 28% aqueous ammonia-ethanol mixed solvent to give 94 mg (85%) of the title compound in the form of light yellow crystals.

$^1$H-NMR (0.1N NaOD) δ: 0.79–1.12 (4H, m), 2.65–2.71 (1H, m), 3.35 (1H, d, J=10.74 Hz), 3.49 (3H, s), 3.60–3.67 (3H, m), 3.83–3.88 (1H, m), 3.98–4.02 (1H, m), 4.58–4.79 (2H, m), 7.58 (1H, d, J=14.64 Hz), 8.42 (1H, s). IR (KBr disk) cm$^{-1}$: 3452, 3072, 2952, 2881, 1726, 1622, 1512, 1446, 1439, 1369, 1352, 1315, 1267. Melting point: 203.2–205.1° C. (decomp.) Elemental analysis data for $C_{19}H_{21}F_2N_3O_4 \cdot 0.25H_2O$: Calcd.: C, 57.35; H, 5.37; N, 10.56 Found : C, 57.56; H, 5.37; N, 10.59 Specific rotation: $[\alpha]_D = -90.45°$ (c=0.995, 0.1 N NaOH solution)

INVENTIVE EXAMPLE 8

7-[3-(S)-tert-Butoxycarbonylamino-4-(S)-fluoromethyl-1-pyrrolidinyl]-1-cyclopropyl-6-fluoro-1,4-fluoro-1,4-dihydro-8-methoxy-4-oxoquinoline-3-carboxylic acid diacetoxyborane complex

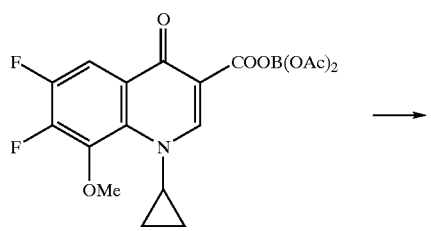

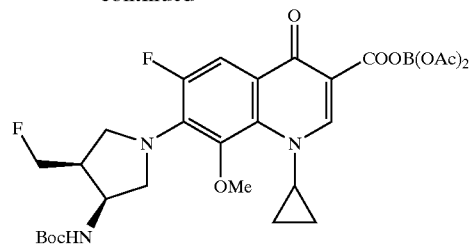

To an acetonitrile (3 ml) solution of 1-cyclopropyl-6,7-difluoro-1,4-dihydro-8-methoxy-4-oxoquinoline-3-carboxylic acid diacetoxyborane complex (423 mg, 1.00 mmol) were added 3-(S)-tert-butoxycarbonylamino-4-(S)-fluoromethylpyrrolidine (327 mg, 1.50 mmol) and triethylamine (280 µl), subsequently carrying out 15 hours of stirring at room temperature. The reaction solution was concentrated under a reduced pressure, and the thus concentrated solution was mixed with chloroform (50 ml) and washed with 10% citric acid aqueous solution and saturated brine in that order. The organic layer was dried over sodium sulfate, the solvent was evaporated, and the thus obtained residue was subjected to a silica gel column chromatography. The crystals obtained from the eluate of chloroform:methanol=97:3 were purified by their recrystallization from a chloroform-n-hexane mixed solvent to give 599 mg (93%) of the title compound in the form of yellow crystals.

$^1$H-NMR (CDCl$_3$) δ: 1.11–1.18 (2H, m), 1.26–1.31 (2H, m), 1.47 (9H, s), 2.05 (6H, s), 2.75–2.83 (1H, m), 3.57 (3H, s), 3.57–3.64 (1H, m), 3.78–3.83 (1H, m), 3.94–4.06 (2H, m), 4.15–4.20 (1H, m), 4.53–4.88 (4H, m), 7.89 (1H, d, J=13.18 Hz), 9.06 (1H, s). IR (KBr disk) cm$^{-1}$: 3318, 2973, 1716, 1631, 1571, 1529, 1446, 1369, 1338, 1274, 1249. Elemental analysis data for $C_{28}H_{32}BF_2N_3O_{10} \cdot 0.5H_2O$: Calcd.: C, 52.58; H, 5.44; N, 6.57 Found : C, 52.51; H, 5.75; N, 6.28 Melting point: 142.4–144.2° C. (decomp.) Specific rotation: $[\alpha]_D = -8.04°$ (c=1.032, chloroform)

INVENTIVE EXAMPLE 9

7-[3-(S)-tert-Butoxycarbonylamino-4-(S)-fluoromethyl-1-pyrrolidinyl]-1-cyclopropyl-6-fluoro-1,4-dihydro-8-methoxy-4-oxoquinoline-3-carboxylic acid

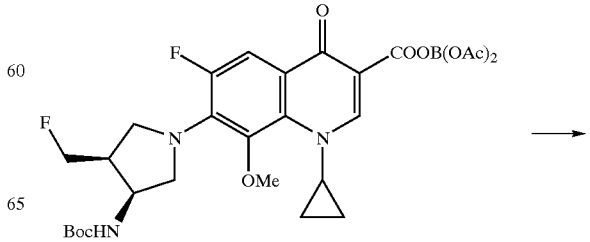

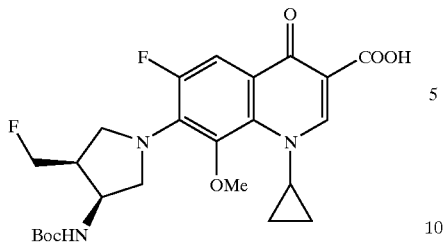

7-[3-(S)-tert-Butoxycarbonylamino-4-(S)-fluoromethyl-1-pyrrolidinyl]-1-cyclopropyl-6-fluoro-1,4-dihydro-8-methoxy-4-oxoquinoline-3-carboxylic acid diacetoxyborane complex (435 mg, 0.70 mmol) was suspended in a mixed solution (10 ml) of ethanol:water=4:1 and mixed with triethylamine (2 ml), and the suspension was heated under reflux for 10 hours. The reaction solution was concentrated under a reduced pressure, and the resulting residue was mixed with chloroform (50 ml) and washed with 10% citric acid aqueous solution and water. The organic layer was dried over sodium sulfate, the solvent was evaporated, and the resulting residue was purified by its recrystallization from an ethanol-n-hexane mixed solvent to give 272 mg (79%) of the title compound in the form of light yellow crystals.

Its data of various instrumental analyses such as $^1$H-NMR and the like coincided with the data described in

INVENTIVE EXAMPLE 6

REFERENCE EXAMPLE 8

3-(S)-Amino-4-(S)-fluoromethylpyrrolidine dihydrochloride

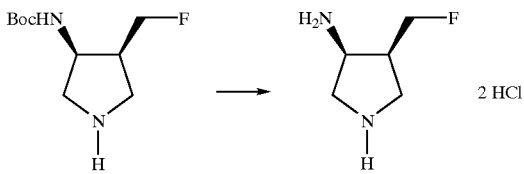

Concentrated hydrochloric acid (1 ml) was added to 3-(S)-tert-butoxycarbonylamino-4-(S)-fluoromethylpyrrolidine (441 mg, 2.02 mmol) which was cooled in an ice bath, and the mixture was stirred for 10 minutes. The reaction solution was mixed with water (5 ml) and washed with dichloromethane (5 ml×3) and diethyl ether (5 ml×1). The aqueous layer was concentrated under a reduced pressure, and the resulting residue was purified by its recrystallization from methanol to give 288 mg (75%) of the title compound in the form of white crystals.

$^1$H-NMR (D$_2$O) δ: 3.07 (1H, br.d, J=33.69 Hz), 3.51–3.61 (2H, m), 3.74 (1H, dd, J=12.69, 7.81 Hz), 3.90 (1H, dd, J=13.18, 7.81 Hz), 4.33 (1H, dd, J=13.18, 7.32 Hz), 4.75–4.99 (2H, m). IR (KBr disk) cm$^{-1}$: 2910, 2594, 2445, 1610, 1581, 1558, 1504, 1450, 1411, 1394, 1375, 1358, 1329, 1308, 1292, 1267, 1242, 1209. Elemental analysis data for C$_5$H$_{11}$FN$_2$.2HCl: Calcd.: C, 31.43; H, 6.83; N, 14.66 Found : C, 31.29; H, 6.87; N, 14.58 Melting point: 198.1–199.0° C. Specific rotation: [α]$_D$=−2.81° (c=1.033, H$_2$O)

INVENTIVE EXAMPLE 10

7-[3-(S)-Amino-4-(S)-fluoromethyl-1-pyrrolidinyl]-1-cyclopropyl-6-fluoro-1,4-dihydro-8-methoxy-4-oxoquinoline-3-carboxylic acid difluoroborane complex

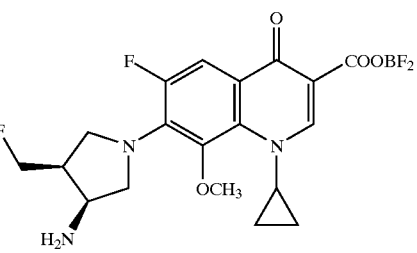

To a dimethyl sulfoxide (2 ml) solution of 1-cyclopropyl-6,7-difluoro-1,4-dihydro-8-methoxy-4-oxoquinoline-3-carboxylic acid difluoroborane complex (343 mg, 1.00 mmol) were added 3-(S)-amino-4-(S)-fluoromethylpyrrolidine dihydrochloride (268 mg, 1.40 mmol) and triethylamine (585 μl), subsequently carrying out 15 hours of stirring at room temperature. The reaction solution was concentrated under a reduced pressure, the thus concentrated solution was mixed with water (100 ml), washed with chloroform (50 ml×3) and then adjusted to pH 6.9 by adding saturated sodium bicarbonate aqueous solution, and the aqueous layer was extracted with chloroform (100 ml×4). The organic layer was dried over sodium sulfate, the solvent was evaporated, and the resulting residue was purified by its recrystallization from ethanol to give 412 mg (92%) of the title compound in the form of light yellow crystals.

$^1$H-NMR (CDCl$_3$) δ: 1.03–1.43 (4H, m), 2.65–2.71 (1H, m), 3.49–3.53 (1H, m), 3.64 (3H, s), 3.72–3.76 (1H, m), 3.77–3.79 (1H, m), 4.05–4.10 (1H, m), 4.26–4.30 (1H, m), 4.76 (2H, br.d, J=46.64 Hz), 7.88 (1H, d, J=13.68 Hz), 8.97 (1H, s). IR (KBr disk) cm$^{-1}$: 3064, 2944, 2889, 1722, 1633, 1566, 1520, 1504, 1444, 1402, 1363, 1329, 1290, 1250, 1220. Elemental analysis data for C$_{19}$H$_{20}$BF$_4$N$_3$O$_4$.0.25H$_2$O: Calcd.: C, 51.20; H, 4.64; N, 9.43 Found : C, 51.00; H, 4.54; N, 9.35 Melting point: 214.1–214.7° C. (decomp.) Specific rotation: [α]$_D$=−125.800 (c=0.996, N,N-dimethylformamide)

INVENTIVE EXAMPLE 11

7-[3-(S)-Amino-4-(S)-fluoromethyl-1-pyrrolidinyl]-1-cyclopropyl-6-fluoro-1,4-dihydro-8-methoxy-4-oxoquinoline-3-carboxylic acid

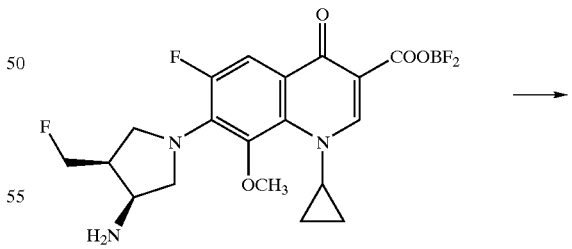

7-[3-(S)-Amino-4-(S)-fluoromethyl-1-pyrrolidinyl]-1-cyclopropyl-6-fluoro-1,4-dihydro-8-methoxy-4-oxoquinoline-3-carboxylic acid difluoroborane complex (348 mg, 781 μmol) was dissolved in a mixed solution (20 ml) of ethanol:water=4:1 and mixed with triethylamine (2 ml), and the mixture was heated under reflux for 4 hours. The solvent was evaporated, and the resulting residue was dissolved by adding concentrated hydrochloric acid and 1N hydrochloric acid, washed with chloroform (50 ml×3) and then, while cooling in an ice bath, alkalified with 50% sodium hydroxide aqueous solution. The aqueous layer was washed with dichloromethane (50 ml×3), adjusted to pH 7.4 with concentrated hydrochloric acid and 1N hydrochloric acid and then extracted with chloroform (100 ml×3). The organic layer was dried over sodium sulfate, the solvent was evaporated, and then the resulting residue was purified by its recrystallization from a 28% aqueous ammonia-ethanol mixed solvent to give 205 mg (67%) of the title compound in the form of light yellow crystals.

Its data of various instrumental analyses such as $^1$H-NMR and the like coincided with the data described in

INVENTIVE EXAMPLE 7

INVENTIVE EXAMPLE 12

7-[3-(S)-Amino-4-(S)-fluoromethyl-1-pyrrolidinyl]-1-cyclopropyl-6-fluoro-1,4-dihydro-8-methoxy-4-oxoquinoline-3-carboxylic acid diacetoxyborane complex

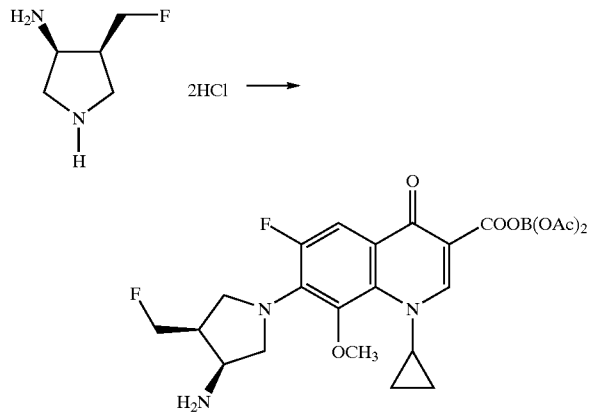

To an acetonitrile (3 ml) solution of 1-cyclopropyl-6,7-difluoro-1,4-dihydro-8-methoxy-4-oxoquinoline-3-carboxylic acid diacetoxyborane complex (423 mg, 1.00 mmol) were added 3-(S)-amino-4-(S)-fluoromethylpyrrolidine dihydrochloride (287 mg, 1.50 mmol) and triethylamine (700 μl), subsequently carrying out 15 hours of stirring at room temperature. The reaction solution was concentrated under a reduced pressure, and the thus obtained residue was mixed with chloroform (50 ml), washed with water and then dried over sodium sulfate. The solvent was evaporated, the resulting residue was subjected to a silica gel column chromatography and then the crystals thus obtained from the eluate of chloroform:methanol=10:1 were washed with ether to give 459 mg (88%) of the title compound in the form of light yellow crystals.

$^1$H-NMR (CDCl$_3$) δ: 1.03–1.41 (4H, m), 2.05 (6H, s), 2.64–2.70 (1H, m), 3.43–3.47 (1H, m), 3.57 (3H, s), 3.68–3.72 (1H, m), 3.83–3.89 (2H, m), 4.02–4.07 (1H, m), 4.17–4.20 (1H, m), 4.67–4.70 (1H, m), 4.79–4.82 (1H, m), 7.87 (1H, d, J=13.19 Hz), 9.04 (1H, s). IR (KBr disk) cm$^{-1}$: 3378, 2931, 2884, 1716, 1627, 1573, 1527, 1446, 1373, 1338, 1280, 1243, 1218. Elemental analysis data for C$_{23}$H$_{26}$BF$_2$N$_3$O$_8$·0.5H$_2$O: Calcd.: C, 52.09; H, 5.13; N, 7.92 Found : C, 52.11; H, 5.36; N, 7.80 Melting point: 182.4–185.6° C. (decomp.) Specific rotation: [α]$_D$=−80.02° (c=1.001, chloroform)

INVENTIVE EXAMPLE 13

7-[3-(S)-Amino-4-(S)-fluoromethyl-1-pyrrolidinyl]-1-cyclopropyl-6-fluoro-1,4-dihydro-8-methoxy-4-oxoquinoline-3-carboxylic acid

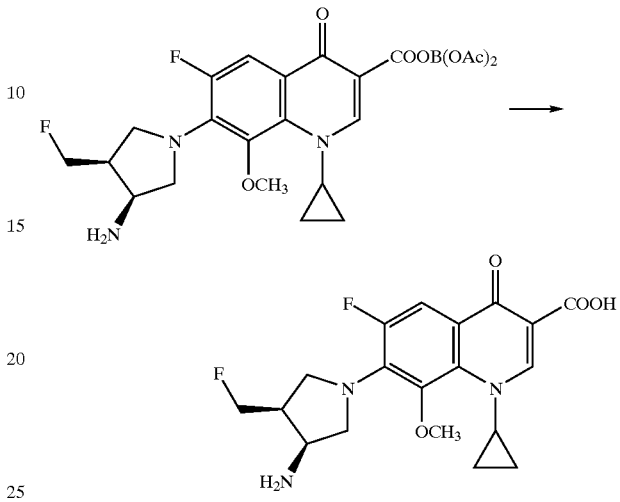

7-[3-(S)-Amino-4-(S)-fluoromethyl-1-pyrrolidinyl]-1-cyclopropyl-6-fluoro-1,4-dihydro-8-methoxy-4-oxoquinoline-3-carboxylic acid diacetoxyborane complex (365 mg, 0.70 mmol) was suspended in a mixed solution (10 ml) of ethanol:water=4:1 and mixed with triethylamine (2 ml), and the mixture was heated under reflux for 14 hours. The reaction solution was concentrated under a reduced pressure, and the thus obtained residue was dissolved by adding concentrated hydrochloric acid and 1 N hydrochloric acid and washed with chloroform (50 ml×3) and then, while cooling in an ice bath, the aqueous layer was alkalified with 50% sodium hydroxide aqueous solution. The aqueous layer was washed with dichloromethane (50 ml×3), adjusted to pH 7.4 with concentrated hydrochloric acid and 1N hydrochloric acid and then extracted with chloroform (100 ml×3). The organic layer was dried over sodium sulfate, the solvent was evaporated, and then the resulting residue was purified by its recrystallization from a 28% aqueous ammonia-ethanol mixed solvent to give 218 mg (81%) of the title compound in the form of light yellow crystals.

Its data of various instrumental analyses such as $^1$H-NMR and the like coincided with the data described in Inventive Example 7.

TABLE 1

Antibacterial activity (minimum inhibitory concentration, μg/ml)

| | Compounds | | |
|---|---|---|---|
| Strains | Ex. 1 | Ex. 2 | Comp. Ex. 1 |
| E. coli, NIHJ | ≤0.003 | ≤0.003 | ≤0.003 |
| S. flexneli, 2A 5503 | 0.006 | 0.006 | 0.013 |
| Pr. vulgaris, 08601 | 0.013 | 0.013 | 0.013 |
| Pr. mirabilis, IFO- 3849 | 0.025 | 0.05 | 0.10 |
| Ser. marcescens, 10100 | 0.05 | 0.05 | 0.10 |
| Ps. aeruginosa, 32104 | 0.20 | 0.20 | 0.20 |
| Ps. aeruginosa, 32121 | 0.05 | 0.10 | 0.10 |
| X. maltophilia, IID 1275 | 0.20 | 0.10 | 0.20 |
| S. aureus, 209P | 0.013 | 0.013 | 0.025 |

TABLE 1-continued

| | Antibacterial activity (minimum inhibitory concentration, μg/ml) | | |
|---|---|---|---|
| | Compounds | | |
| Strains | Ex. 1 | Ex. 2 | Comp. Ex. 1 |
| S. epidermidis, 56500 | 0.05 | 0.05 | 0.10 |
| Str. pyogenes, G-36 | 0.10 | 0.10 | 0.20 |
| Str. faecalis, ATCC-19433 | 0.10 | 0.10 | 0.20 |
| S. aureus, 870307 | 0.20 | 0.39 | 0.78 |

Industrial Applicability

Thus, as has been described in the foregoing, the compound of the present invention is possessed of excellent antibacterial activity and safety, so that it is useful as medicaments.

What is claimed is:

1. A compound represented by the following formula (I), a salt thereof, or a hydrate thereof:

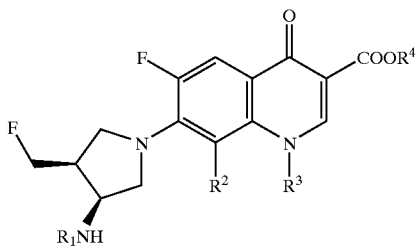

wherein $R^1$ represents a hydrogen atom or an alkyl group having 1 to 6 carbon atoms, wherein said alkyl group may have one or more substituents selected from the group consisting of a hydroxyl group, a halogen atom, an alkylthio group having 1 to 6 carbon atoms and an alkoxyl group having 1 to 6 carbon atoms, $R^2$ represents a halogenomethoxyl group or an alkoxyl group having 1 to 6 carbon atoms, $R^3$ represents an alkyl group having 1 to 6 carbon atoms, an alkenyl group having 2 to 6 carbon atoms, a halogenoalkyl group having 1 to 6 carbon atoms, a cyclic alkyl group having 3 to 6 carbon atoms which may have a substituent, a heteroaryl group which may have a substituent, an alkoxyl group having 1 to 6 carbon atoms or an alkylamino group having 1 to 6 carbon atoms, and $R^4$ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxylmethyl group having 2 to 7 carbon atoms or a phenylalkyl group composed of an alkylene group having 1 to 6 carbon atoms and a phenyl group.

2. The compound, the salt thereof, or the hydrate thereof according to claim 1, wherein $R^1$ in the formula (I) is a hydrogen atom.

3. The compound, the salt thereof, or the hydrate thereof according to claim 1, wherein $R^2$ in the formula (I) is a methoxyl group.

4. The compound, the salt thereof, or the hydrate thereof according to claim 1, wherein $R^3$ in the formula (I) is a cyclopropyl group.

5. The compound, the salt thereof, or the hydrate thereof according to claim 1, wherein $R^3$ in the formula (I) is a halogenocyclopropyl group.

6. The compound, the salt thereof, or the hydrate thereof according to claim 1, wherein $R^3$ in the formula (I) is a 1,2-cis-halogenocyclopropyl group.

7. The compound, the salt thereof, or the hydrate thereof according to claim 1, wherein $R^3$ in the formula (I) is a stereochemically pure substituent.

8. The compound, the salt thereof, or the hydrate thereof according to claim 1, wherein $R^3$ in the formula (I) is a (1R,2S)-2-halogenocyclopropyl group.

9. The compound, the salt thereof, or the hydrate thereof according to claim 1, wherein $R^3$ in the formula (I) is a (1R,2S)-2-fluorocyclopropyl group.

10. The compound, the salt thereof, or the hydrate thereof according to claim 1, wherein the compound of formula (I) is a stereochemically pure compound.

11. An antibacterial agent which comprises a compound described in any one of claims 1 to 10 or 22–23, a hydrate thereof, a salt thereof or a hydrate of the salt thereof, as an active ingredient.

12. 7-[3-(S)-Amino-4-(S)-fluoromethyl-1-pyrrolidinyl]-1-cyclopropyl-6-fluoro-1,4-dihydro-8-methoxy-4-oxoquinoline-3-carboxylic acid, a salt thereof, or a hydrate thereof.

13. 7-[3-(S)-Amino4-(S)-fluoromethyl-1-pyrrolidinyl]-6fluoro-1-[2-(S)-fluoro-1-(R)-cyclopropyl]-1,4-dihydro-8-methoxy-4-oxoquinoline-3-carboxylic acid, a salt thereof, or a hydrate thereof.

* * * * *